US011807854B2

(12) United States Patent
Wong et al.

(10) Patent No.: US 11,807,854 B2
(45) Date of Patent: Nov. 7, 2023

(54) CD44 APTAMER

(71) Applicant: The Chinese University of Hong Kong, Shatin (CN)

(72) Inventors: Nathalie Wong, Fo Tan (CN); Wing Sze Lo, Tin Shui Wai (CN); James Y.W. Lau, Ma On Shan (CN)

(73) Assignee: The Chinese University of Hong Kong, Hong Kong SAR (CN)

( * ) Notice: Subject to any disclaimer, the term of this patent is extended or adjusted under 35 U.S.C. 154(b) by 0 days.

(21) Appl. No.: 17/694,482

(22) Filed: Mar. 14, 2022

(65) Prior Publication Data

US 2022/0364094 A1 Nov. 17, 2022

Related U.S. Application Data

(60) Provisional application No. 63/188,965, filed on May 14, 2021.

(51) Int. Cl.
*C12N 15/115* (2010.01)
*C12Q 1/6834* (2018.01)
*C12N 15/10* (2006.01)
*C12Q 1/6816* (2018.01)

(52) U.S. Cl.
CPC ........ *C12N 15/115* (2013.01); *C12N 15/1048* (2013.01); *C12Q 1/6816* (2013.01); *C12Q 1/6834* (2013.01); *C12N 2310/16* (2013.01); *C12N 2310/315* (2013.01); *C12N 2330/31* (2013.01)

(58) Field of Classification Search
None
See application file for complete search history.

*Primary Examiner* — Sean McGarry
(74) *Attorney, Agent, or Firm* — Kilpatrick Townsend & Stockton LLP

(57) ABSTRACT

The present invention provides an aptamer that specifically hinds CD44, composition comprising the aptamer, as well as methods for detecting CD44 and for targeted delivery to CD44-expressing cells.

20 Claims, 14 Drawing Sheets

Specification includes a Sequence Listing.

CD44 APTAMER

RELATED APPLICATIONS

This application claims priority to U.S. Provisional Patent Application No. 63/188,965, filed May 14, 2021, the contents of which are hereby incorporated by reference in the entirety for all purposes.

REFERENCE TO SUBMISSION OF A SEQUENCE LISTING AS A TEXT FILE

The Sequence Listing written in file 080015-1287634-033110US_SL.txt created on Jun. 24, 2022, 1,051 bytes, machine format IBM-PC, MS-Windows operating system, is hereby incorporated by reference in its entirety for all purposes.

BACKGROUND OF THE INVENTION

The CD44 antigen is a cell-surface glycoprotein involved in cell—cell interactions, cell adhesion and migration. CD44 is expressed in a large number of mammalian cell types. The standard isoform, designated CD44s, comprising exons 1-5 and 16-20, is expressed in most cell types. CD44 splice variants containing variable exons are designated CD44v. Some epithelial cells also express a larger isoform (CD44E), which includes exons v8-10. CD44 is a receptor for hyaluronic acid and can also interact with other ligands, such as osteopontin, collagens, and matrix metalloproteinases (MMPs). Due to its participation in a wide variety of important cellular functions including lymphocyte activation, recirculation and homing, hematopoiesis, and tumor metastasis, CD44 is a cell surface molecule that is attracting increased attention.

Chemical antibodies, termed aptamers, have been increasingly utilized for clinical applications in the past few decades. One aptamer, pegaptanib (an anti-VEGF aptamer), has been approved by the FDA, and several more are currently in clinical trials. Increased interest in the use of aptamers for therapy is due to several reasons, including the fact that they exhibit no immunogenicity, little batch-to-batch variation due to being chemically synthesized, and are more stable than conventional antibodies. Thanks to their small size, they also show superior tumor penetration. The most important advantage is that these aptamers can be attached to nanoparticles, drugs, imaging agents, or other nucleic acid therapeutics without loss-of-function. This functionalization capacity is leading to new and more targeted therapies, with fewer side effects than current treatment modalities. When compared to conventional treatment, which is largely a passive process, targeted delivery systems are much more effective. For an aptamer to be an effective drug delivery agent, the aptamer must bind to its target on the cell surface and be internalized within a short period of time. Thus, there is a pressing need for aptamers with improved binding characteristics and cell penetration capability in research and therapeutic applications. The present invention fulfills this and other related needs by providing a new aptamer that binds CD44 with high affinity and specificity as well as by providing compositions and methods useful for detecting CD44-expressing cells or for targeted delivery of an imaging or therapeutic agent to CD44-positive cells.

BRIEF SUMMARY OF THE INVENTION

The invention resides in the construction of a novel aptamer and the revelation of its desirable characteristics of high affinity and specificity to cell surface antigen CD44 variants E and s. These findings also provide new compositions and methods for the use of this aptamer in detection of CD44E or CD44s isoforms and in targeted delivery to CD44-positive cells. Thus, in the first aspect, the present invention provides a novel aptamer, which comprises an oligonucleotide having the sequence set forth in SEQ ID NO:1 and which specifically binds CD44 variants E and s.

In some embodiments, the aptamer further comprises a heterologous moiety such as a detectable moiety or a therapeutic agent or a solid support. In some embodiments, the aptamer consists essentially of the nucleotide sequence of SEQ ID NO:1 and a detectable moiety, or the aptamer consists essentially of the nucleotide sequence of SEQ ID NO:1 and a therapeutic agent. For example, the aptamer consists of the nucleotide sequence of SEQ ID NO:1 and a detectable moiety or the aptamer consists of the nucleotide sequence of SEQ ID NO:1 and a therapeutic agent. In some embodiments, the oligonucleotide having the sequence set forth in SEQ ID NO:1 comprises at least one chemical modification, for example, the phosphodiester bonds in the nucleotide sequence are modified to phosphorothioate linkage by substituting the non-bridging oxygen atoms in the phosphodiester bonds to sulfur atoms. In some cases, all of the phosphodiester bonds are modified. In some cases, only some of the phosphodiester bonds, for example, those connecting the 1, 2, 3, 4, or 5 bases at the 3' and/or 5' end of the oligonucleotide are replaced. In some embodiments, the aptamer immobilized to a solid substrate, e.g., by the 3' or 5' end, or by another reactive group on the oligonucleotide. In some embodiments, the aptamer binds CD44 with an equilibrium dissociation constant KD of less than about 10 nM or less than about 5 nM, e.g., about 3.30 nM.

In a related aspect, the present invention provides a composition comprising the aptamer described above and herein and a pharmaceutically acceptable excipient. The composition may be formulated for systemic administration, such as by oral ingestion or by injection, or the composition may be formulated for local administration, such as by topical application or by suppository. In some cases, the aptamer comprises a phosphorothioate-modified oligonucleotide.

In a second aspect, the present invention provides a method for detecting the presence of CD44-expressing cells. The method comprises these steps: (1) contacting a plurality of cells potentially comprising CD44-expressing cells with the aptamer described above and herein under conditions permissible for specific binding between the aptamer and CD44; and (2) detecting cells specifically bound to the aptamer and identifying such cells as CD44-expressing cells.

In some embodiments, the plurality of cells are present in a biological sample taken from a person, for example, a blood sample or a biopsy sample. In some embodiments, the plurality of cells are present in a person's body. In some embodiments, the aptamer comprises a detectable moiety or an imaging agent, which allows for ready detection, for example, real-time imaging of the distribution of CD44+ cells, especially CD44+ cancer stem cells. In some embodiments, the aptamer is immobilized to a solid substrate. In some embodiments, the method further includes a step subsequent to step (2) to isolate the cells specifically bound to the aptamer and identified as CD44-bearing cells, such as CD44-bearing cancer cells.

In a third aspect, a method is provided for targeted delivery to CD44-expressing cells. The method comprises administering to a patient in need thereof an effective amount of the aptamer comprising an imaging or therapeutic agent as described above and herein, for example, to treat a patient diagnosed to have a type of cancer expressing CD44 on the cancer cell surface. In some embodiments, the oligonucleotide of the aptamer is a phosphorothioate-modified oligonucleotide.

In some embodiments, the aptamer is administered systemically. In some embodiments, the aptamer is administered locally. In some embodiments, the aptamer consists essentially of SEQ ID NO:1 and the imaging or therapeutic agent, or the aptamer consists of SEQ ID NO:1 and the imaging or therapeutic agent. In some embodiments, the therapeutic agent is an anti-cancer drug. In some embodiments, the oligonucleotide of the aptamer is a phosphorothioate-modified oligonucleotide.

BRIEF DESCRIPTION OF THE DRAWINGS

Identification and characterization of CD44E/s aptamers. FIG. 1A also shows the establishment of CD44E- and CD44s-dual-overexpressed HCC stable cell line (CD44E/s). Gene expression of CD44E (E) and CD44s (s) in HKCI-C1 vector control (CN) and CD44E/s cells were determined by real-time quantitative PCR and compared between the two cell lines. For CD44 protein expression, 20 ug of total protein of either CN or CD44E/s cell lysates were resolved on a 5-12% gradient acrylamide gel. Membrane with proteins transferred from the gel was blotted with anti-CD44 or anti-GAPDH antibodies. GAPDH protein was used as endogenous loading control. Relative quantity of CD44E to CD44s protein (E:s) was determined based on the their protein band intensities.

Serum stability and drug guiding capability of CD44-Apt1.

In vivo homing and non-toxic nature of CD44-Apt1.

DEFINITIONS

Figure 1A:
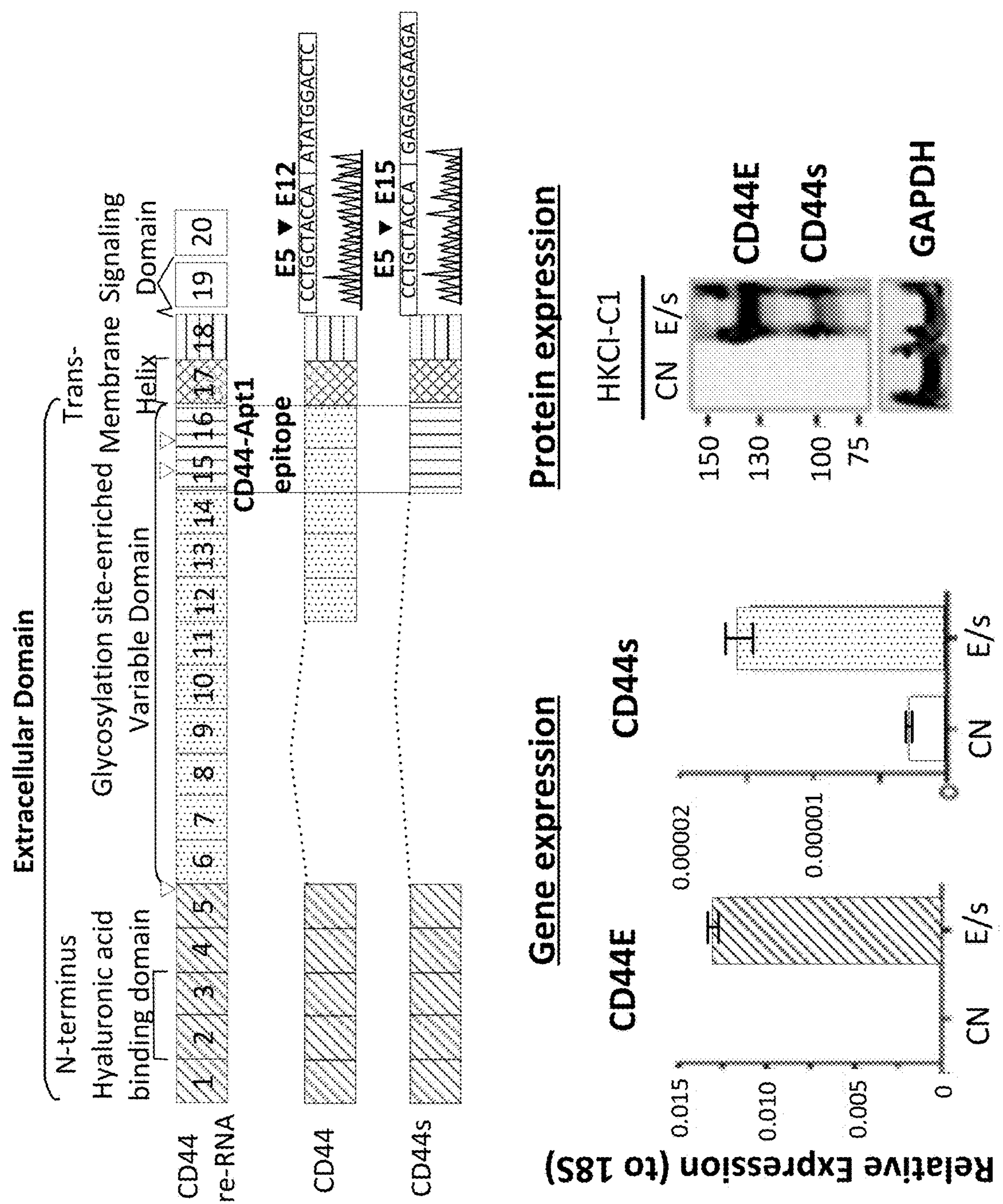
(FIG. 1A) Gene structure and protein domain arrangement of CD44 and two prevalent isoforms CD44E and CD44s in HCC. CD44 consists of 20 exons. Exons 1-5 (yellow box) and 15-18 encode the standard isoform CD44s and are conserved in both isoforms. Exons 1-15 depict the extracellular domain with Exons 2-3 for the hyaluronan binding domain and Exons 6-14 (green box) for the variant domain harboring abundant glycosylation sites. Exon 17 (grey box) is for transmembrane helical domain, while Exon 18 (blue box) encodes the intracellular signaling transduction domain. Exons 19 and 20 (grey open box) are mutually exclusive exons. This figure depicts two short nucleotide sequences for CD44E (E5-E12) and CD44s (E5-E15), where alternative splicing between Exons 5 and 12 resulted in the CD44E isoform and between Exons 5 and 15 resulted in the CD44s isoform. Supporting sequencing traces for the detection of CD44s and CD44E isoforms in HCC are provided. Epitope region bound by CD44-Apt1 is also suggested. Grey inverse triangles indicate reported MMP cleavage sites on CD44 protein.

The term "comprise," including variations such as "comprises" or "comprising", is used to imply the inclusion of a stated step or element or integer or group of steps or elements or integers but not the exclusion of any other step or element or integer or group of elements or integers.

The term "consists of" or "consisting of" is used to mean that a method, process or composition of matter (e.g., aptamer sequence) has the recited steps and/or components and no additional steps or components.

The term "consists essentially of" or "consisting essentially of" in the context of a nucleic acid sequence as used herein is to be construed non-exhaustively and is understood to mean a nucleotide sequence wherein additional nucleotide bases may be present wherein said additional bases constitute no more than about 10% of the total nucleotide sequence or, in the alternative, no more than additional 1, 2, 3, 4, or 5 nucleotide bases, for example, at either 3' or 5' end of the nucleotide sequence. When an aptamer is described as "consisting essentially of" an oligonucleotide sequence conjugated to a moiety, the aptamer should not include any additional components that would materially change the fundamental function or utility of the aptamer: for example, an aptamer "consisting essentially of" an oligonucleotide sequence and a detectable moiety should not include another moiety that confers another function such as a second detection signal or a therapeutic activity. On the other hand, an aptamer "consisting essentially of" an oligonucleotide sequence and a detectable moiety does not exclude chemical modifications that improve stability of the conjugate.

As used herein, the term "aptamer" or "oligonucleotide aptamer" refers in general to an oligonucleotide of a single defined sequence (e.g., SEQ ID NO:1), which is optionally conjugated with an additional moiety (such as a detectable moiety, a therapeutic agent, or a solid substrate) and/or optionally includes chemical modification, and which retains the properties of binding specifically to CD44. Typically, an "aptamer" is a single-stranded nucleic acid. Structurally, the aptamers of the present disclosure are specifically binding oligonucleotides. Aptamers may comprise RNA, DNA or both RNA and DNA. The aptamer may be synthetically produced using well-known methods. Alternatively, the aptamer may be recombinantly produced.

The term "oligonucleotide" sequence and "nucleotide" sequence are used herein interchangeably to generically refer to polydeoxyribonucleotides (containing 2'-deoxy-D-ribose or modified forms thereof), i.e., DNA, to polyribonucleotides (containing D ribose or modified forms thereof), i.e., RNA, and to any other type of polynucleotide, which is an N-glycoside or C-glycoside of a purine or pyrimidine base, or modified purine or pyrimidine base or abasic nucleotides. According to the present disclosure, the term "oligonucleotide" includes not only those with conventional nucleobases, sugar residues, and internucleotide linkages, but also those that contain modifications of any one or more of these three components. For example, an oligonucleotide sequence of SEQ ID NO:1 encompasses the phosphorothioate-modified version of the sequence in which the phosphodiester bonds connecting the individual nucleotides are replaced with phosphorothioate (PS) bonds by substituting a sulfur atom for a non-bridging oxygen in the phosphate backbone of an oligonucleotide. This modification renders the internucleotide linkage resistant to nuclease degradation. In some cases, phosphorothioate bonds can be introduced between the last 3-5 nucleotides at the 5'- and/or 3'-end of the oligonucleotide sequence.

As used herein, the term "binding affinity" refers to the tendency of an aptamer to bind or not bind a target and describes the measure of the strength of the binding or affinity of the aptamer to bind the target. The energetics of said interactions are significant in "binding affinity" because they define the necessary concentrations of interacting partners, the rates at which these partners are capable of associating, and the relative concentrations of bound and free molecules in a solution. The energetics are characterized herein through, among other ways, by the determination of a dissociation constant, Kd. As is known in the art, a low dissociation constant indicates stronger binding and affinity of the molecules to each other.

As used herein, the term "biological sample" refers to a cell or population of cells or a quantity of tissue or fluid from a subject. Often, a "biological sample" will contain cells from the subject. Biological samples include, but are not limited to, tissue biopsies, needle biopsies, scrapes (e.g., buccal scrapes), whole blood as well as acellular and cellular fractions of the blood (i.e., plasma, serum, blood cells), lymph, bone marrow, urine, stool, saliva, sputum, primary or permanent cell culture, spinal fluid, pleural fluid, pericardial fluid, ascitic fluid, or cerebrospinal fluid. Samples may be paraffin-embedded or frozen tissue.

The term "conjugated with" or "coupled to" encompasses any construction whereby the aptamer is covalently linked, attached, or joined at its 3' or 5' terminal or at any side reactive group to an agent that may serve as a detectable moiety or a therapeutically active agent for the purpose of detecting or imaging of target cells or tissue or for the purpose of treating a medical condition.

The term "isolated" as used herein is intended to refer to the aptamer purified from other components or chemicals which may be present during the process of generating and purifying the aptamer (e.g., using the SELEX method). In the context of cells, the term also refers to cells isolatable or purified from other components in the environment in which it may naturally occur. The isolated cell may be purified to any degree relative to its naturally-obtainable state.

As used herein, the term "specifically binds" indicates that the aptamer reacts or associates more frequently, more rapidly, with greater duration, and/or with greater affinity with a particular cell or substance than it does with alternative cells or substances. For example, an aptamer that specifically binds to a target protein such as CD44 binds that protein or an epitope or immunogenic fragment thereof with greater affinity, avidity, more readily, and/or with greater duration than it binds to unrelated protein and/or epitopes or immunogenic fragments thereof. Although "specific binding" does not necessarily require exclusive binding or non-detectable binding of another molecule, this term is defined by the comparative dissociation constants (Kd) of the aptamer for its intended target as compared to the dissociation constant with respect to the aptamer and other materials in the environment or unrelated molecules in general. Typically, the Kd for the aptamer with respect to the target will be less than 1/100, such as less than 1/200 or 1/500 or 1/1000 of the Kd with respect to the target and the unrelated material or accompanying material in the environment. In some cases, the Kd may be 1/10,000, 1/100,000 or 1/1,000,000 or less.

The term "treat" or "treating," as used in this application, describes an act that leads to the elimination, reduction, alleviation, reversal, prevention and/or delay of onset or recurrence of any symptom of a predetermined medical condition. In other words, "treating" a condition encompasses both therapeutic and prophylactic intervention against the condition, including facilitation of patient recovery from the condition. In the context of the present invention, the term "treat" or "treatment" or "treating" is understood to mean administering a therapeutically effective amount of the aptamer or pharmaceutical composition as disclosed herein and reducing at least one symptom of a clinical condition caused by, associated with, or exacerbated by CD44 expression.

The term "effective amount," as used herein, refers to an amount of a substance that produces a desired effect (e.g., an detectable imaging signal or an inhibitory or suppressive effect on the growth or proliferation or metastasis of target cells) for which the substance (e.g., an aptamer of this invention) is used or administered. In some cases, the effects include the prevention, inhibition, or delaying of any pertinent biological process to any detectable extent. The exact amount will depend on the nature of the substance (the active agent), the manner of use/administration, and the purpose of the application, and will be ascertainable by one skilled in the art using known techniques as well as those described herein.

The terms "carrier" and "excipient" refer to compositions of matter that are conventionally used in the art to facilitate the storage, administration, and/or the biological activity of an active compound (see, e.g., Remington's Pharmaceutical Sciences, 16th Ed., Mac Publishing Company (1980). A carrier may also reduce any undesirable side effects of the active compound. For example, a suitable carrier is stable, e.g., incapable of reacting with other ingredients in the carrier. In one example, the carrier does not produce significant local or systemic adverse effect in recipients at the dosages and concentrations employed for treatment.

As used herein, the term "heterologous" is used to describe the relationship of two elements placed adjacent to each other in a construct, referring to these two elements such as two polynucleotide sequences (e.g., a promoter sequence or a polypeptide-encoding sequence) or two polypeptide sequences (e.g., signal sequence and another peptide sequence) being from two different natural origins, such that these two elements are not found in the same relative positions in nature. Thus, a "heterologous promoter" of a gene refers to a promoter that is not naturally operably linked to that gene. Similarly, a "heterologous polypeptide" or "heterologous polynucleotide" to one particular protein or its encoding sequence is one derived from an origin different from the protein's origin. The fusion of two heterologous polypeptide (or polynucleotide) sequences does not result in a longer polypeptide (or polynucleotide) sequences that can be found in nature as an intact protein (or naturally occuring nucleotide sequence) or a segment thereof.

As used herein, the term "about" denotes a range of value that is +/−10% of a specified value. For instance, "about 10" denotes the value range of 9 to 11 (10+/−1).

DETAILED DESCRIPTION OF THE INVENTION

I. General

Basic texts disclosing general methods and techniques in the field of recombinant genetics include Sambrook and Russell, *Molecular Cloning, A Laboratory Manual* (3rd ed. 2001); Kriegler, *Gene Transfer and Expression: A Laboratory Manual* (1990); and Ausubel et al., eds., *Current Protocols in Molecular Biology* (1994).

For nucleic acids, sizes are given in either kilobases (kb) or base pairs (bp). These are estimates derived from agarose or acrylamide gel electrophoresis, from sequenced nucleic acids, or from published DNA sequences. For proteins, sizes are given in kilodaltons (kDa) or amino acid residue numbers. Proteins sizes are estimated from gel electrophoresis, from sequenced proteins, from derived amino acid sequences, or from published protein sequences.

Oligonucleotides that are not commercially available can be chemically synthesized, e.g., according to the solid phase phosphoramidite triester method first described by Beaucage & Caruthers, *Tetrahedron Lett.* 22: 1859-1862 (1981), using an automated synthesizer, as described in Van Devanter et. al., *Nucleic Acids Res.* 12: 6159-6168 (1984). Purification of oligonucleotides is performed using any art-recognized strategy, e.g., native acrylamide gel electrophoresis or anion-exchange HPLC as described in Pearson & Reanier, *J. Chrom.* 255: 137-149 (1983). Polynucleotide sequences such as synthetic oligonucleotides can be verified using well-established methodologies, e.g., the chain termination method for sequencing double-stranded templates of Wallace et al., *Gene* 16: 21-26 (1981).

II. Aptamers

Aptamers are molecules that have been known for the past two decades. Several unique properties of aptamers make them attractive tools for use in a wide array of molecular biology applications and as potential pharmaceutical agents. First, most aptamers bind to targets with high affinity, demonstrating typical dissociation constants in the pico- to nanomolar range. Binding sites for aptamers include clefts and grooves of target molecules resulting in antagonistic activity very similar to many currently available pharmaceutical agents. Second, aptamers are structurally stable across a wide range of temperatures and storage conditions, maintaining the ability to form their unique tertiary structures. Third, aptamers can be chemically synthesized, in contrast to the expensive and work-intensive biological systems needed to produce monoclonal antibodies.

Disclosed herein are aptamer molecules that specifically bind to the CD44 antigen and therefore can be used for effective intracellular delivery of agents, such as chemotherapy molecules to treat cancer cells expressing CD44. Such aptamer molecules of the present disclosure are particularly useful as detection agents as well as diagnostic and therapeutic agents.

Aptamers are single stranded oligonucleotides or oligonucleotide analogs that bind to a particular target molecule, such as a protein or a small molecule. Thus, aptamers are the oligonucleotide analogy to antibodies. In general, aptamers comprise about 15 to about 100 nucleotides, or about 15 to about 50 nucleotides, or about 20 to about 40 nucleotides, in that oligonucleotides of a length that falls within these ranges can be prepared by conventional techniques.

Aptamer binding is highly dependent on the secondary structure formed by the aptamer oligonucleotide. Both RNA and single stranded DNA (or analog) aptamers are known. See, for example, Burke et al. (1996). *J. Mol. Biol.* 264: 650-666; Ellington and Szostak (1990). *Nature* 346:818-22; Hirao et al. (1998). *Mol Divers.* 4:75-89; Jaeger et al. (1998). *EMBO Journal* 17:4535; Kensch et al. (2000). *J. Biol. Chem* 275:18271-8; Schneider et al. (1995). *Biochemistry* 34:9599-9610; and U.S. Pat. Nos. 5,773,598; 6,028,186; 6,110,900; 6,127,119; and 6,171,795.

Various methods for preparing aptamers according to the present disclosure will be familiar to persons skilled in the art. Systematic Evolution of Ligands by Exponential Enrichment, "SELEX™" is a method for making a nucleic acid ligand for any desired target, as described, e.g., in U.S. Pat. Nos. 5,475,096 and 5,270,163, and WO91/19813. SELEX™ technology is based on the fact that nucleic acids have sufficient capacity for forming a variety of two- and three-dimensional structures and sufficient chemical versatility available within their monomers to act as ligands (i.e., form specific binding pairs) with virtually any chemical compound, whether large or small in size.

The method involves selection from a mixture of candidates and step-wise iterations of structural improvement, using the same general selection theme, to achieve virtually any desired criterion of binding affinity and selectivity. Starting from a mixture of nucleic acids, preferably comprising a segment of randomized sequence, the SELEX™ method includes steps of contacting the mixture with the target under conditions favorable for binding, partitioning unbound nucleic acids from those nucleic acids which have bound to target molecules, dissociating the nucleic acid-target pairs, amplifying the nucleic acids dissociated from the nucleic acid-target pairs to yield a ligand-enriched mixture of nucleic acids, then reiterating the steps of binding, partitioning, dissociating and amplifying through as many cycles as desired.

Within a nucleic acid mixture containing a large number of possible sequences and structures, there is a wide range of binding affinities for a given target. A nucleic acid mixture comprising, for example, a 20-nucleotide randomized segment can have 420 candidate possibilities. Those which have the higher affinity constants for the target are most likely to bind to the target. After partitioning, dissociation and amplification, a second nucleic acid mixture is generated, enriched for the higher binding affinity candidates. Additional rounds of selection progressively favor the best ligands until the resulting nucleic acid mixture is predominantly composed of only one or a few sequences. These can then be cloned, sequenced and individually tested for binding affinity as pure ligands.

Cycles of selection and amplification are repeated until a desired goal is achieved. In the most general case, selection/amplification is continued until no significant improvement in binding strength is achieved on repetition of the cycle. The method may be used to sample as many as about 1018 different nucleic acid species. The nucleic acids of the test mixture preferably include a randomized sequence portion as well as conserved sequences necessary for efficient amplification. Nucleic acid sequence variants can be produced in a number of ways including synthesis of randomized nucleic acid sequences and size selection from randomly cleaved cellular nucleic acids. The variable sequence portion may contain fully or partially random sequence; it may also contain subportions of conserved sequence incorporated with randomized sequence. Sequence variation in test nucleic acids can be introduced or increased by mutagenesis before or during the selection/amplification iterations.

Enrichment of aptamer candidates during selection may be monitored using restriction fragment length polymorphism (RFLP) and flow cytometry as described in Shigdar S et al. (2013) *Cancer Letters* 330:84-95.

III. Aptamer Characteristics and Modification

The binding affinity describes the measure of the strength of the binding or affinity of molecules to each other. Binding affinity of the aptamer herein with respect to targets and other molecules is defined in terms of Kd. The dissociation constant can be determined by methods known in the art and can be computed even for complex mixtures by methods such as those, for example, set forth in Caceci, M., et al., *Byte* (1984) 9:340-362. Examples of measuring dissociation constants are described for example in U.S. Pat. No. 7,602,495 which describes surface Plasmon resonance analysis, and in U.S. Pat. No. 6,562,627, and US 2012/00445849. In another example, the Kd is established using a double-filter nitrocellulose filter binding assay such as that disclosed by Wong and Lohman, (1993). *Proc. Natl. Acad. Sci. USA* 90, 5428-5432. Methods for determining binding affinity of aptamers is also described in for example, Stoltenburg R et al. (2005) *Anal Bioanal Chem* 383:83-91, Tran D T et al (2010) *Molecules* 15, 1127-1140, and Cho M. et al. (2013) *Proc. Natl. Acad. Sci. USA* 110(46):18460-18465.

It has been observed that for some small oligonucleotides, direct determination of Kd is difficult, and can lead to misleadingly high results. Under these circumstances, a competitive binding assay for the target molecule or other candidate substance can be conducted with respect to substances known to bind the target or candidate. The value of the concentration at which 50% inhibition occurs (Ki) is, under ideal conditions, equivalent to Kd. However, in no event will a Ki be less than Kd. Thus, determination of Ki, in the alternative, sets a maximal value for the value of Kd. Under those circumstances where technical difficulties preclude accurate measurement of Kd, measurement of Ki can conveniently be substituted to provide an upper limit for Kd. A Ki value can also be used to confirm that an aptamer of the present disclosure binds CD44.

One potential problem encountered in the use of nucleic acids as therapeutics in that oligonucleotides in their phosphodiester form may be quickly degraded in body fluids by intracellular and extracellular enzymes such as endonucleases and exonucleases before the desired effect is manifest. The present disclosure also includes analogs as described herein and/or additional modifications designed to improve one or more characteristics of the aptamers such as protection from nuclease digestion.

Oligonucleotide aptamer modifications contemplated in the present disclosure include, but are not limited to, those which provide other chemical groups that incorporate additional charge, polarizability, hydrophobicity, hydrogen bonding, electrostatic interaction, and fluxionality to the nucleic acid ligand bases or to the nucleic acid ligand as a whole.

Modifications to generate oligonucleotide aptamers that are resistant to nucleases can also include one or more substitute internucleotide linkages, altered sugars, altered bases, or combinations thereof. Such modifications include 2'-position sugar modifications, 5-position pyrimidine modifications, 8-position purine modifications, modifications at exocyclic amines, substitution of 4-thiouridine, substitution of 5-bromo or 5-iodo-uracil, backbone modifications, phosphorothioate or alkyl phosphate modifications, methylations, and unusual base-pairing combinations such as the isobases isocytidine and isoguanosine; 3' and 5' modifications such as capping; conjugation to a high molecular weight, non-immunogenic compound; conjugation to a lipophilic compound; and phosphate backbone modification.

In one example, the non-immunogenic, high molecular weight compound conjugated to the aptamer of the present disclosure is polyalkylene glycol, preferably polyethylene glycol. In one example, the backbone modification comprises incorporation of one or more phosphorothioates into the phosphate backbone. In another example, the aptamer of the present disclosure comprises the incorporation of fewer than 10, fewer than 6, or fewer than 3 phosphorothioates in the phosphate backbone.

Where appropriate, additional modification may include at least one of the following, 2'-deoxy, 2'-halo (including 2'-fluoro), 2'-amino (preferably not substituted or mono- or disubstituted), 2'-mono-, di- or tri-halomethyl, 2'-O-alkyl, 2'-O-halo-substituted alkyl, 2'-alkyl, azido, phosphorothioate, sulfhydryl, methylphosphonate, fluorescein, rhodamine, pyrene, biotin, xanthine, hypoxanthine, 2,6-diamino purine, 2-hydroxy-6-mercaptopurine and pyrimidine bases substituted at the 6-position with sulfur or 5 position with halo or C15 alkyl groups, abasic linkers, 3'-deoxy-adenosine as well as other available “chain terminator” or “non-extendible” analogs (at the 3'-end of the RNA), or labels such as $^{32}P$, $^{33}P$ and the like. All of the foregoing can be incorporated into an aptamer using the standard synthesis techniques disclosed herein.

IV. Use of Aptamers

Solid tumors are composed of mutually interacting cancer cells and tumor microenvironment. Many environmental components, such as extracellular matrix (ECM), mesenchymal stem cells, endothelial and immune cells, and various growth factors and cytokines, provide signals, either stimulatory or inhibitory, to cancer cells and determine their fates. Meanwhile, cancer cells can also educate surrounding cells or tissues to undergo changes that are in favorable of tumor progression. CD44, a transmembrane receptor for hyaluronic acid (HA) and many other ECM components and a co-receptor for growth factors and cytokines, is a critical cell surface molecule that can sense, integrate, and transduce cellular microenvironmental signals to membrane-associated cytoskeletal proteins or to cell nucleus to regulate a variety of gene expressions that govern cell behaviors. Mounting evidence suggests that CD44, particularly CD44v isoforms, are cancer stem cell (CSC) markers and critical regulators of cancer stemness, including self-renewal, tumor initiation, and metastasis. Thus, CD44 is widely used alone or in combination with other cell surface markers to isolate or enrich CSCs through fluorescence-activated cell sorting of dissociated single cells that originate from the patient, xenograft tumor tissues, or tumor cell cultures. Sorted cells are cultured in a specialized culture medium for spheroid formation or inoculated into immunodeficient mice for the analysis of tumorigenic or metastatic potential. Thus, the aptamer molecules of this invention can be used as affinity ligands to separate and purify target molecules (e.g., CD44 or CD44-expressing cancer cells), as probes to trace, monitor, detect and quantitate target molecules (e.g., CD44 or CD44-expressing cancer cells), or to block, allow, activate or catalyze reactions that are physiologically relevant to achieve therapeutic effect. They can act as pharmaceutical agent, bind to a specific target and direct specific molecules to a desired site.

The aptamer molecules of the present disclosure can be used in in vitro processes, for example, affinity purification mixtures to purify target molecules (e.g., CD44 or CD44-expressing cancer cells). The aptamers are useful for chromatographic separations of target molecules (e.g., CD44 or CD44-expressing cancer cells) from contaminants and for purifying target molecules from cell cultures or cell extracts.

In one example, the aptamer molecules of the present disclosure can be used as a capture agent to bind or immobilize a target (e.g., CD44 or CD44-expressing cancer cells) to a solid support or substrate. The solid support can be comprised of substrates having the structure and composition commonly associated with filters, wafers, wafer chips, membranes, and thin films. It is further contemplated that the solid support may comprise any material depending of the desired use, including but not limited to resins, affinity resins, glass, metal surfaces and materials such as steel, ceramic or polymeric materials (e.g., polyethylene, polypropylene, polyamide, and polyvinylidenefluoride etc. or combinations thereof), magnetic or polymer beads, or any diagnostic detection reagent, to capture or immobilize reagents for diagnostic, detection or quantitative studies.

The aptamers of the present disclosure can be used in vitro for diagnostic and/or detection purposes to determine the presence of cells expressing CD44 on their surface, for example, CD44-bearing cancer cells in malignant tissue. The method involves examining a biological sample for the presence of CD44+ cancer stem cells. For example, the biological sample can be contacted with a labelled aptamer of the present disclosure and the ability of the aptamer to specifically bind to the cells in the sample is determined. Binding indicates the presence of a CD44-bearing cancer stem cell. The aptamer of the present disclosure can also be used to localize a tumor in vivo by administering to a subject an aptamer of the present invention, labelled with a reporter group giving off a detectable signal. Bound aptamers can then be detected using flow cytometry, microscopy, external scintigraphy, emission tomography, optical imaging or radionuclear scanning. The method can be used to stage a cancer in a subject with respect to the extent of the disease and to monitor changes in response to therapy.

Detection of cancer stem cells can be facilitated by coupling the aptamer to a detectable label or moiety. Examples of detectable labels include various enzymes, prosthetic groups, fluorescent materials, luminescent materials, bioluminescent materials, electron dense labels, labels for MRI, and radioactive materials. Examples of suitable enzymes include horseradish peroxidise, alkaline phosphatise, β-galactosidase, or acetylcholinesterase. Examples of suitable prosthetic group complexes include streptavidin/biotin and avidin/biotin. Examples of suitable fluorescent materials include umbellifone, fluorescein isothiocyanate, rhodamine, dischlorotriazinylamine fluorescein, dansyl chloride or phycoerythrin. An example of a luminescent material includes luminol. Examples of bioluminescent materials include luciferase, luciferin, and aequorin, and examples of suitable radioactive material include $^{125}I$, $^{131}I$, $^{35}S$, $^{18}F$, $^{64}Cu$, $^{94}mTc$, $^{124}I$, $^{11}C$, $^{13}N$, $^{15}O$, $^{68}Ga$, $^{86}Y$, $^{82}Rb$ or $^{3}H$.

Labelling at the 3' end of the aptamer can be achieved, for example, by templated extension using Klenow polymerase, by T4 ligase-mediated ligation, and by terminal deoxynucleotidyl transferase. Labelling at the 5' end can be achieved by the supplementation of the in vitro transcription mix with an excess of GTP-β-S, the thiol of which can then be used to attach biotin. In addition, direct chemical conjugation of a suitable group(s) to either 5'- or 3'-end can be used to label the aptamers.

The oligonucleotide sequence of the aptamers of the present disclosure can be linked to a moiety and direct the moiety to CD44+ cells, such as CD44+ cancer stem cells. Examples of moieties include toxins, radionuclides, or chemotherapeutic agents, which can be used to kill cancer stem cells.

The aptamer can be fused to the moiety, e.g., the toxin, either by virtue of the moiety and aptamer being chemically synthesized, or by means of conjugation, e.g., a non-peptide covalent bond, or a non-amide bond, which is used to join separately produced aptamer and the moiety. Alternatively, the aptamer and moiety may be joined by virtue of a suitable linker molecule including but not limited to a peptide.

Useful toxin molecules include peptide toxins, which are significantly cytotoxic when present intracellularly. Examples of toxins include cytotoxins, metabolic disrupters (inhibitors and activators) that disrupt enzymatic activity and thereby kill cancer stem cells, and radioactive molecules that kill all cells within a defined radius of the effector portion. A metabolic disrupter is a molecule, e.g., an enzyme or a cytokine that changes the metabolism of a cell such that is normal function is altered. Broadly, the term toxin includes any effector that causes death to a tumor cell (e.g., a CD44-bearing cancer cell).

Many peptide toxins have a generalized eukaryotic receptor binding domain; in these instances the toxin must be modified to prevent killing cells not bearing CD44 (e.g., to prevent killing cells not bearing CD44 but having a receptor for the unmodified toxin). Such modifications must be made in a manner that preserves the cytotoxic function of the molecule. Potentially useful toxins include, but are not limited to diphtheria toxin, cholera toxin, ricin, 0-Shiga-like toxin (SLT-I, SLT-II, SLT-IIV), LT toxin, C3 toxin, Shiga toxin pertussis toxin, tetanus toxin, *Pseudomonas* exotoxin, alorin, saponin, modeccin and gelanin. Other toxins include tumor necrosis actor alpha (TNF-alpha) and lymphotoxin (LT). Another toxin having antitumor activity is calicheamicin gamma 1, a diyne-ene containing antitumor antibiotic with considerable potency against tumors, see, e.g., Zein N. et al (1988). Science 240:1198-1201.

The aptamer and the toxin moiety can be linked in any of several ways known to those of skill in the art. For example, a method of conjugating an aptamer to a toxin (gelonin) is described in Chu T C et al. (2006) *Cancer Res* 6(12)5989-5992. The moiety coupled to the oligonucleotide sequence can also be a modulator of the immune system that either activates or inhibits the body's immune system at the local level. For example, cytokines (e.g., lymphokines such as IL-2) delivered to a tumor can cause the proliferation of cytotoxic T-lymphocytes or natural killer cells in the vicinity of the tumor.

The moiety or reporter group can also be a radioactive molecule, for example, a radionucleotide, or a so-called sensitizer, e.g., a precursor molecule that becomes radioactive under specific conditions, e.g., boron when exposed to a bean of low-energy neutrons, in the so-called "boron neutron capture therapy" (BNCT) as described in Barth et al., (1990). *Scientific American* October 1990:100-107. Compounds with such radioactive effector portions can be used both to inhibit proliferation of cancer stem cells in the tumor and to label the cancer stem cells for imaging purposes.

Radionucleotides are single atom radioactive molecules that can emit either α, β, or γ particles. α particle emitters are preferred to β or γ particle emitters, because they release far higher energy emissions over a shorter distance, and are therefore efficient without significantly penetrating, and harming, normal tissues. Suitable α particle-emitting radionuclides include $^{211}$At, $^{212}$Pb, and $^{212}$Bi. The radioactive molecule may be tightly linked to the aptamer either directly or by a bifunctional chelate. This chelate must not allow elution and thus premature release of the radioactive molecule in vivo, see. Waldmann, *Science,* 252:1657-62 (1991).

Suitable chemotherapeutic agents that may be attached to the apatmer of the present disclosure may be selected from doxorubicin, taxol, cytochalasin B, gramicidin D, ethidium bromide, emetine, mitomycin, etoposide, tenoposide, vincristine, vinblastine, colchicin, doxorubicin, daunorubicin, dihydroxy anthracin dione, mitoxantrone, mithramycin, actinomycin D, 1 de-hydrotestosterone, glucocorticoids, procaine, tetracaine, lidocaine, propranolol, and puromycin, antimetabolites (such as methotrexate, 6-mercaptopurine, 6 thioguanine, cytarabine, fludarabin, 5-fluorouracil, decarbazine, hydroxyurea, asparaginase, gemcitabine, cladribine), alkylating agents (such as mechlorethamine, thioepa, chlorambucil, melphalan, carmustine (BSNU), lomustine (CCNU), cyclophosphamide, busulfan, dibromomannitol, streptozotocin, dacarbazine (DTIC), procarbazine, mitomycin C, cisplatin and other platinum derivatives, such as carboplatin), antibiotics (such as dactinomycin (formerly actinomycin), bleomycin, daunorubicin (formerly daunomycin), idarubicin, mithramycin, mitomycin, mitoxantrone, plicamycin, anthramycin (AMC)).

Alternatively, the moiety is a chemotherapeutic molecule or other molecule that is capable of intercalating into the stem region sequence of the aptamer. For example, where the chemotherapeutic molecule is doxorubicin, the molecule is capable of intercalating at CpG sites in the DNA of the aptamer stem. Chemotherapeutic agents such as doxorubicin are intrinsically fluorescent which makes them convenient for probing and visualizing their location with various imaging technologies. The therapeutic and imaging capabilities combined in a DOX molecule make it suitable for use as a theranostic agent. Accordingly, the aptamers of the present disclosure can be used as theranostic agents to deliver doxorubin to cancer stem cells. In order to increase aqueous solubility, the amino group of the sugar in doxorubicin can be protonated by forming a DOX hydrochloride.

Moieties that are capable of intercalating into the aptamers of the present disclosure include, doxorubicin, adriamycine, berberine, provflavine, mitoxantrone, daunorubicin, thalidomide, dactinomycin, danomycin, actinomycin D, 9-aminoacridine, amrubicin, amsacrine, anthramycine, berbine, bleomycin, elliplicine, epirubicin, idarubicin, methpyrillo, mithramycin, mitomycin, mitomycin C, mitoxantrone, mitoxantrone, pirarubicin, pixantrone, plicamycin, proflavine, prodigiosin, thalidomide, voreloxin, valrubicin, zorubicin. chlorpheniramine, prodisiosin, methapyrillino, mitomycin, distamycin, dantinomycin, distamycin, carboplatin, cisplatin and other platinum derivatives, Hoechst 33258, berenil, DAPI or carcinogenic agents (including the exo 8,9 epoxide of aflatoxin B1, acridines such as proflavine or quinacrine or ethidium bromide). Other GC intercalating agents will be familiar to a person skilled in the art of the present invention and are intended to be included within the scope of the present disclosure.

The aptamer of the present disclosure can also be used for siRNA, ribozyme, or DNAzyme delivery into cells. Specific choices of suitable siRNA, ribozyme or therapeutic agent will depend upon the circumstances. Examples of siRNAs or ribozymes that are suitable for use according to the present disclosure include those which target ATP binding cassette membrane transporters, stemness genes (Bmi-1, Notch 1, Sox 2, Oct-4, Nanog, .beta.-catenin, Smo, nestin, ABCG2, Wnt2 and SCF, etc), GAPDH (glyceraldehyde 3-phosphate dehydrogenase), and survivin.

The aptamers of the present invention can also be used to deliver cargo into CD44+ cancer stem cells in a variety of solid tumors. Gelonin is a ribosomal toxin that can inhibit the process of protein synthesis and is cytotoxic. However, it is membrane impermeable and needs an usher for its cellular entry. Thus, the aptamers of this invention can be utilized to deliver membrane impermeable toxic payload to cancer stem cells. In another embodiment the aptamers of the present invention can be used to deliver Doxorubicin (DOX), a DNA intercalating chemotherapeutic agent that is unable to target cancer stem cells on its own, to CD44+ cancer stem cells.

The present invention also extends to the use of the aptamer molecules as the so-called theranostics, or simultaneous drug delivery and imaging agents. This can be achieved by conjugating the aptamer to the surface of a fluorescent quantum dot (QD). Next, the QD-aptamer conjugate is incubated with Dox to form the QD-aptamer-Dox nanoparticle. Both Dox and QD are fluorescent molecules. Due to their proximity in the QD-aptamer-Dox nanoparticle, however, they quench each other's fluorescence by a bi-fluorescence resonance energy transfer (FRET) mechanism. Thus, the QD-aptamer-Dox nanoparticle is non-fluorescent. Upon internalization of the QD-aptamer-Dox nanoparticle via PSMA-mediated endocytosis in prostate cancer cells, Dox is released from the QD-aptamer-Dox nanoparticles, resulting in the recovery of fluorescence by both Dox and QD.

V. Pharmaceutical Compositions

The present disclosure further provides a pharmaceutical composition comprising the aptamer, which may include a detectable moiety, a diagnostic or therapeutic agent as described herein. A pharmaceutical composition of the present disclosure includes composition prepared for storage or administration that include a pharmaceutically effective amount of the aptamer in a pharmaceutically acceptable carrier and/or excipient. The choice of excipient or other elements of the composition can be adapted in accordance with the route and device used for administration.

Suitable carriers for use in practicing the present invention may include those conventionally used, for example, water, saline, aqueous dextrose, lactose, Ringer's solution a buffered solution, hyaluronan and glycols are exemplary liquid carriers, particularly (when isotonic) for solutions. Suitable pharmaceutical carriers and excipients include starch, cellulose, glucose, lactose, sucrose, gelatin, malt, rice, flour, chalk, silica gel, magnesium stearate, sodium stearate, glycerol monostearate, sodium chloride, glycerol, propylene glycol, water, ethanol, and the like. Other general additives such as anti-oxidative agent, buffer solution, bacteriostatic agent etc. can be added. In order to prepare injectable solutions, pills, capsules, granules, or tablets, diluents, dispersing agents, surfactants, binders and lubricants can be additionally added.

The aptamers of the disclosure and formulations thereof may be administered systemically (e.g., by oral ingestion or by injection intravenously, intramuscularly, or subcutaneously) or administered directly or topically (e.g., locally) to the patient or target tissue or organ as is generally known in the art. For example, a composition can comprise a delivery vehicle, including liposomes, for administration to a subject. Nucleic acid molecules can be administered to cells by a variety of methods known to those of skill in the art, including, but not restricted to, encapsulation in liposomes, by iontophoresis, or by incorporation into other vehicles, such as biodegradable polymers, hydrogels, cyclodextrins poly (lactic-co-glycolic) acid (PLGA) and PLCA microspheres, biodegradable nanocapsules, and bioadhesive microspheres, or by proteinaceous vectors.

Delivery systems to be used with the aptamers of the present disclosure include, for example, aqueous and non-aqueous gels, creams, multiple emulsions, microemulsions, liposomes, ointments, aqueous and non-aqueous solutions, lotions, aerosols, hydrocarbon bases and powders, and can contain excipients such as solubilizers, permeation enhancers (e.g., fatty acids, fatty acid esters, fatty alcohols and amino acids), hydrophilic polymers (e.g., polycarbophil and polyvinylpyrolidone), and the like. In some cases, the pharmaceutically acceptable carrier is a liposome or a transdermal enhancer.

A pharmaceutical composition of the disclosure is in a form suitable for administration, e.g., systemic or local administration, into a cell or subject, including a mammal such as a human being. Suitable forms, in part, depend upon the use or the route of entry, for example, oral, transdermal, or by injection. Other factors are known in the art, and include considerations such as toxicity and forms that prevent the composition from exerting its effect.

The aptamer or composition comprising the aptamer of this invention can be administered parenterally (for example, intravenous, hypodermic, local or peritoneal injection). The effective dosage of the aptamer can be determined according to weight, age, gender, health condition, diet, administration frequency, administration method, excretion and severity of a disease. Generally, an amount between 0.1 mg/kg and 100 mg/kg body weight/day of the aptamer is administered.

Formulations for oral use can also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example, peanut oil, liquid paraffin, or olive oil.

Aqueous suspensions contain the aptamer in a mixture with excipients suitable for the manufacture of aqueous suspensions. Such excipients are suspending agents, for example, sodium carboxymethylcellulose, methylcellulose, hydropropyl-methylcellulose, sodium alginate, polyvinylpyrrolidone, gum tragacanth and gum acacia; dispersing or wetting agents can be a naturally-occurring phosphatide, for example, lecithin, or condensation products of an alkylene oxide with fatty acids, for example, polyoxyethylene stearate, or condensation products of ethylene oxide with long chain aliphatic alcohols, for example, heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example, polyethylene sorbitan monooleate. The aqueous suspensions can also contain one or more preservatives, for example, ethyl, or n-propyl p-hydroxybenzoate, one or more colouring agents, one or more flavouring agents, and one or more sweetening agents, such as sucrose or saccharin.

Oily suspensions can be formulated by suspending the aptamer in a vegetable oil, for example, arachis oil, olive oil, sesame oil or coconut oil, or in a mineral oil such as liquid paraffin. The oily suspensions can contain a thickening agent, for example, beeswax, hard paraffin or cetyl alcohol. Sweetening agents and flavoring agents can be added to provide palatable oral preparations. These compositions can be preserved by the addition of an anti-oxidant such as ascorbic acid.

Dispersible powders and granules suitable for preparation of an aqueous suspension by the addition of water provide the aptamer in admixture with a dispersing or wetting agent, suspending agent and one or more preservatives. Suitable dispersing or wetting agents or suspending agents are exemplified by those already mentioned above. Additional excipients such as sweetening, flavoring and coloring agents can also be present.

Pharmaceutical compositions of the invention can also be in the form of oil-in-water emulsions. The oily phase can be a vegetable oil or a mineral oil or mixtures of these. Suitable emulsifying agents can be naturally-occurring gums, for example, gum acacia or gum tragacanth, naturally-occurring phosphatides, for example, soy bean, lecithin, and esters or partial esters derived from fatty acids and hexitol, anhydrides, for example, sorbitan monooleate, and condensation products of the partial esters with ethylene oxide, for example, polyoxyethylene sorbitan monooleate. The emulsions can also contain sweetening and flavoring agents.

A sterile injectable preparation can also be a sterile injectable solution or suspension in a non-toxic parenterally acceptable diluent or solvent, for example, as a solution in 1,3-butanediol. Among the acceptable vehicles and solvents that can be employed are water, Ringer's solution, isotonic sodium chloride solution, and an isotonic salt solution containing sodium and potassium chloride. In addition, sterile, fixed oils are conventionally employed as a solvent or suspending medium. For this purpose, any bland fixed oil can be employed including synthetic mono- or diglycerides. In addition, fatty acids such as oleic acid find use in the preparation of injectables.

It is understood that the specific dose level for any particular subject depends upon a variety of factors including the activity of the specific compound employed, the age, body weight, general health, sex, diet, time of administration, route of administration, and rate of excretion, drug combination and the severity of the particular disease undergoing therapy. The administration frequency may be one to several times a day, weekly, or monthly.

EXAMPLES

The following examples are provided by way of illustration only and not by way of limitation. Those of skill in the art will readily recognize a variety of non-critical parameters that could be changed or modified to yield essentially the same or similar results.

BACKGROUND

Aptamers are single-stranded synthetic DNA or RNA oligonucleotides that can fold into stable, unique three-dimensional structure for specific docking onto targeted molecules via structural recognition with high affinity and dissociation constants as low as pico- to nano-molar range [1]. Compared to protein antibodies, aptamer is non-immunogenic in nature. It could be denatured at high temperature for a brief period then fold back into functional three-dimensional structure and is thus incredibly thermal stable. With its small size, usually ranging 1-50 kDa, it could be efficiently internalized into cells upon binding to specific cell surface targets, like CD44-Apt1 in this invention, via clathrin- and caveolae-dependent endocytosis[2], and shows powerful penetrating ability[3]. Aptamers could be cost-effectively and time-efficiently synthesized in large-scale by solid phase synthesis[4]. Due to nucleic acid in nature, aptamers could be easily chemically modified with high plasticity[5]. Aptamer-based therapeutics have hence attracted much attention in clinical applications, for instance linking with nanoparticles or reporter molecules for diagnostics and imaging[6], or itself acting as antagonist or conjugated with anti-cancer drug for therapeutic purposes [7].

METHODS AND RESULTS

Figure 1B:
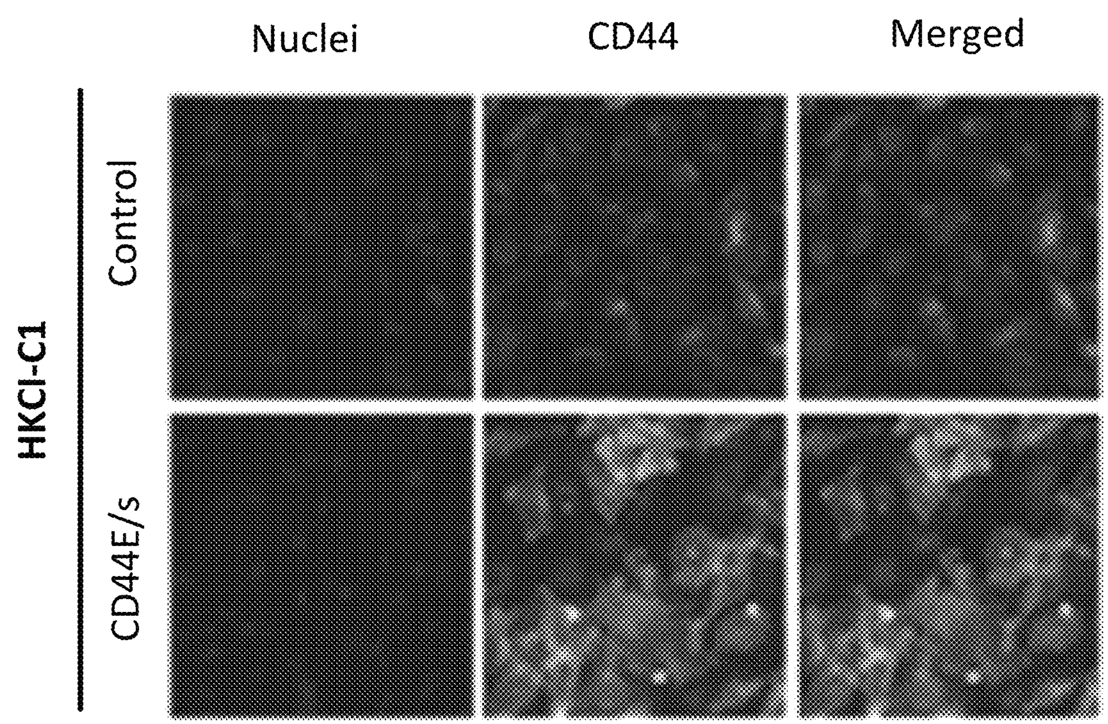
(FIG. 1B) Immunofluorescence analysis of CD44 expression in the HKCI-C1 cells. CD44 protein (green) in the CN and CD44E/s cells was stained with primary CD44 antibody and Alexa fluor-488 labeled secondary antibody. Nuclei were stained with Hoechst (blue).

To identify aptamers targeting CD44, the present inventors utilized the Loss-Gain Cell-based Systematic Evolution of Ligands by Exponential Enrichment (Cell-SELEX) technique[8]. The loss-gain cell-SELEX consists of two steps, one is the gain step, also known as positive selection, in which both CD44 aptamers and non-specific bound aptamers will be captured, and the other is the loss step, or so-called negative selection, in which the non-specific bound aptamers from the gain step will be removed. This loss-gain step will be repeated up to 11 cycles to enrich the CD44-specific aptamers gradually exponentially from cycle to cycle. At first, a single-stranded aptamer library was synthesized as a central randomized sequence of 40 nucleotides flanked by 18-base known primer hybridization sequences at both ends. A stable HCC cell line with constitutively overexpression of CD44E and CD44s variants (HKCI-C1 CD44E/s) was generated. A vector-control cell line was also produced using the same HCC cell line (HKCI-C1 CN). Both gene and protein expressions of CD44E and CD44s were successfully overexpressed in the CD44E/s cell line (FIG. 1A). Immunofluorescent staining using CD44 antibody also supported the overexpression (FIG. 1B).

To start the Loss-Gain Cell-SELEX, in the first two cycles, the aptamer library was applied to the CD44E/s cells and incubated to allow aptamer binding. After incubation, non-bound aptamers were washed off and the cells with bound aptamers were collected. Bound aptamers were recovered and amplified by polymerase chain reaction (PCR) using primers priming to the hybridization sequences on the aptamer. The reverse primer is conjugated with biotin at its 5' end, while the forwards primer without attachment. The amplified double-stranded aptamer pool with biotin-labeled on the negative stands were captured using streptavidin-magnetic beads. After isolation and washing, the positive-stranded aptamers were eluted and separated from the negative strands using high concentration of sodium hydroxide. The single stranded aptamer pool was purified using silica-membrane-based column. This purified aptamer pool was then used to start the next selection cycle. Starting from cycle three and onwards, a loss step was added before the gain step. The aptamers from last cycle were firstly applied to the prewashed vector-control cells and incubated to deplete the aptamers that bind to proteins expressed by the cell line itself. The aptamer supernatant from the loss step was then put on to the CD44E/s cells for target binding. The aptamers bound to CD44E/s were thus enriched and amplified from cycle to cycle. The gain-loss cell-SELEX was repeated for 11 cycles. Aptamer pools from alternative cycles starting from the first cycle were sequenced by the next-generation sequencing. Obtained aptamer sequences were counted and analyzed.

Figure 1C:
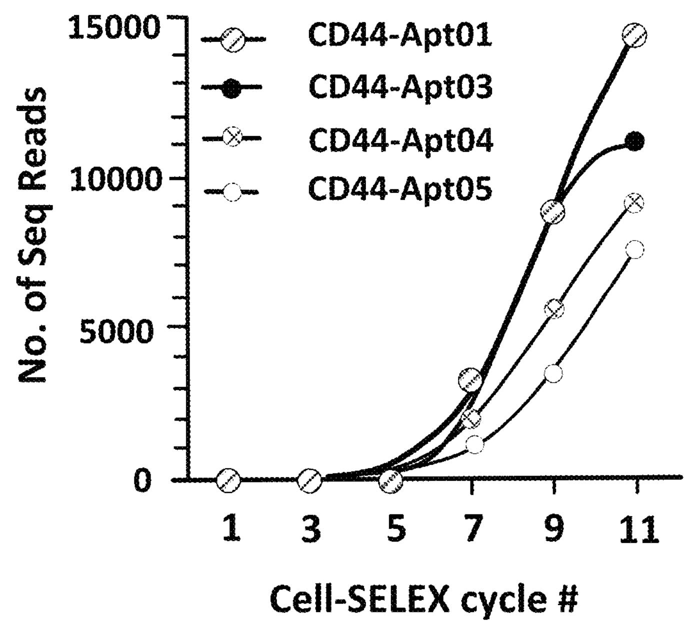
(FIG. 1C) Enrichment of CD44-specific aptamer sequences by the technique of loss-gain CELL-SELEX. Aptamer pools from alternative cycles during Cycle 1 to 11 were sequenced by the next-generation sequencing. For the top eight abundant aptamers, named CD44-Apt1 to -Apt8, number of sequencing reads in different cycles were plotted to illustrate their gradual enrichment across the SELEX process.
Figure 1D:
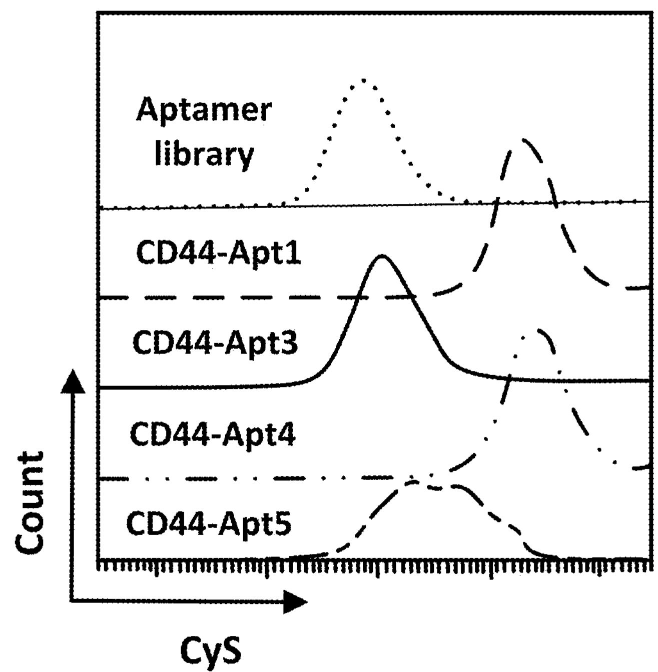
(FIG. 1D) Flow cytometric analysis of HKCI-C1 CD44E/s cells after incubation with Apt-1 to -Apt5 and library control. These 5 aptamers and aptamer library were conjugated with Cy5 fluorescence and incubated with HKCI-C1 CD44E/s cells at 200 nM for 1 hour at room temperature with agitation before analyzing by flow-cytometry.
Figure 1E:
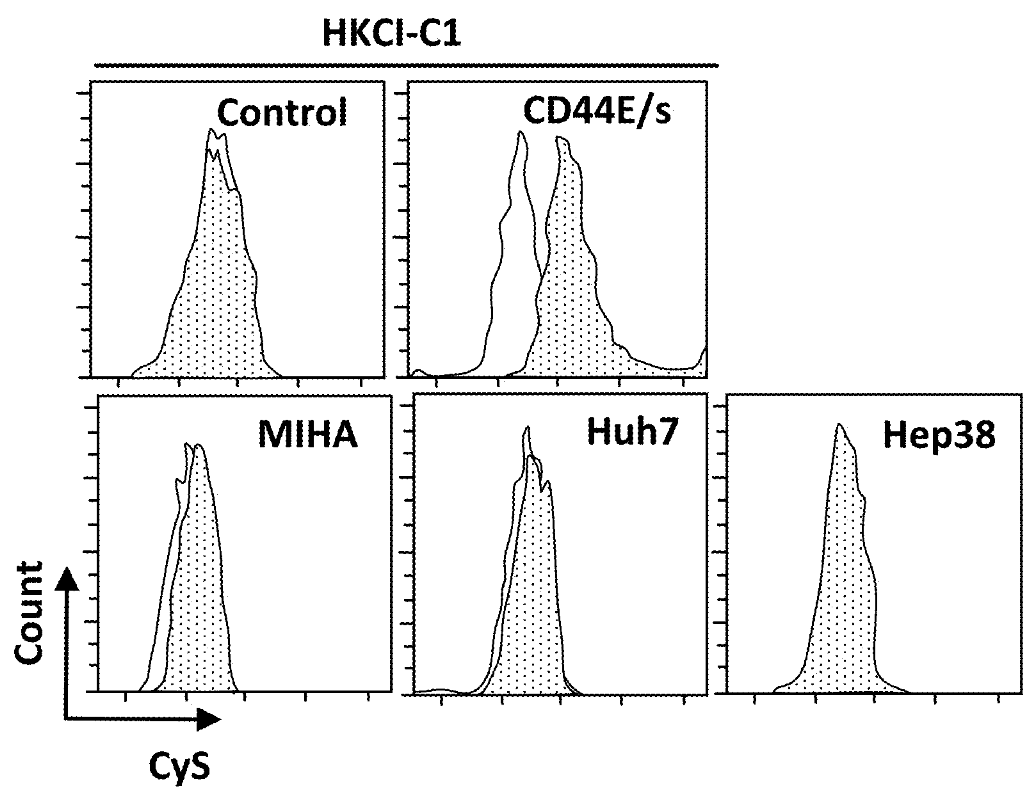
(FIG. 1E) Flow cytometric analysis of various human liver cells after incubation with Cy5-labelled CD44-Apt1 aptamer. HKCI-C1 cells, including vector control and CD44E/s, and a normal liver cell line MIHA, and two CD44-negative HCC cell lines, Huh7 and Hep3B cell lines were stained with Cy5-labeled CD44-Apt1 or library control and analyzed by flow cytometry.
Figure 1F:
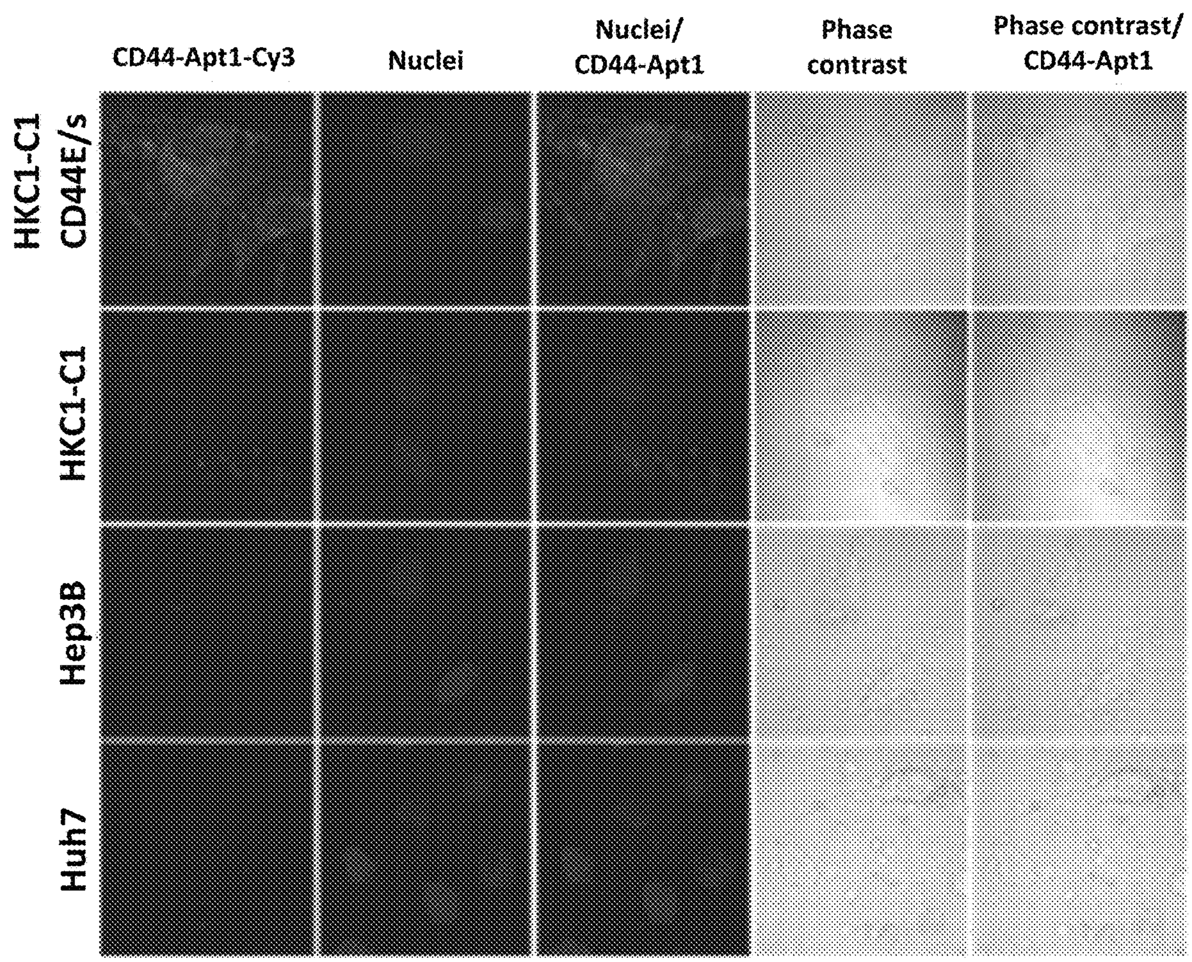
(FIG. 1F) Confocal fluorescence microscopy of HCC cells for localization of CD44-Apt1. HKCI-C1 vector control and CD44E/s cells, Hep3B, and Huh7 were live-stained with Cy3-labeled CD44-Apt1 (red), and then fixed and imaged by confocal microscopy. Nuclei were stained using Hoechst (blue). Phase-contrast images were taken to illustrate the outline of cells.

Based on the sequencing results, four aptamers, named CD44-Apt1, -Apt3, -Apt4, and -Apt5 were ascendingly enriched across cycles (FIG. 1C). They were conjugated with Cy5 fluorophore and stained the CD44E/s cells. The stained cells were then analyzed by flow cytometry (FIG. 1D). Compared to the staining with library control, CD44E/s cells stained with either one of the four Cy5-conjugated CD44 aptamers all accumulated more Cy5 signal, resulted in signal shifting to the right (FIG. 1D). Since CD44-Apt1 was the most abundant aptamer after 11 cycles of selections, it was chosen to be further studied. The binding specificity of CD44-Apt1 was further accessed (FIG. 1E). Three cell lines with negligible CD44 expression, including a normal liver cell line MIHA and two live cancer cell lines Hep3B and Huh7, were stained with the Cy5-CD44-Apt1 or the aptamer library. Flow cytometric analysis of the stained cells showed no shift in Cy5 signal between the two staining, suggesting no non-specific binding by the CD44-Apt1. In another experiment, a Cy3-labeled CD44-Apt1 and a nuclei dye Hoechst were used to stain cells, including CD44E/s, vector control, Hep3B, and Huh7. The cells were then visualized using immunofluorescence confocal imaging (FIG. 1F). With the CD44E/s cells, CD44-Apt1 localization was apparent not only on the cell membrane but also into the cytoplasmic and nuclear compartments. Of HKCI-C1 vector control cells, both CD44E and CD44s genes were negligible with minimal CD44-Apt1 detected inside the vector control cells. With the CD44-negative cells Hep3B and Huh7, consistent with the flow cytometry analysis, CD44-Apt1 binding was not observed. Both flow cytometric analysis and confocal imaging suggested high specificity of CD44-Apt1 to CD44 variant proteins.

Figure 1G:
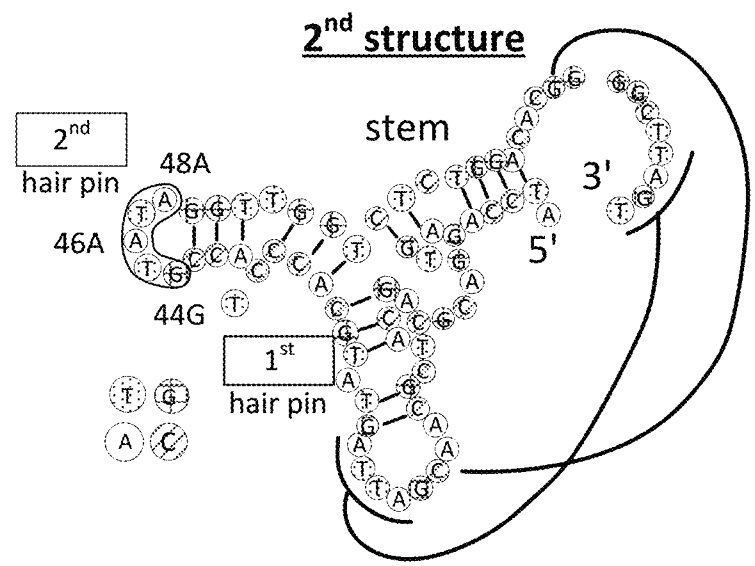
(FIG. 1G) Predicted secondary and tertiary structure of CD44-Apt1. One dot represents one nucleotide, with red, blue, black, and green dots denoting the nucleotide T, C, G, and A, respectively. Black lines indicate the nucleotide interaction between the loop of first hair pin and the sequence at the most 3' end when Apt1 folded into 3D structure. Based on the predicted structure, 5 nucleotides from 44G to 48A in the loop of the second hair pin are unmasked and do not interact with any part of the rest of the sequence. The nucleotides 44G, 46A and 48A were therefore labeled with biotin and used for the epitope mapping experiment.
Figure 1G:
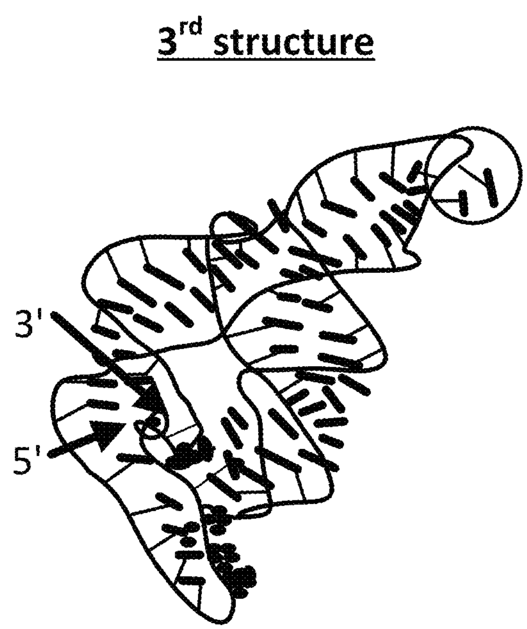

Based on the sequence of CD44-Apt1 (Table 1), secondary structure prediction suggested the CD44-Apt1 forming two hair pins and one stem with a minimum free energy of −19.7 kcal/mol (FIG. 1G). This secondary structure was used to simulate the tertiary folding of the CD44-Apt1. The tertiary folding revealed interaction of the loop region of the first hair pin and the distal sequence at the 3' end. The loop of the second hair spin from nucleotide 44G to 48A is completely exposed and is an ideal region for biotin labelling that is required for the following binding affinity experiment. Although the 14-base sequence at the most 3' end seems like a free fragment based on the secondary structure prediction, this sequence buries at the core of the whole aptamer based on the tertiary folding prediction and it interacts with the bases in the loop of the first hairpin. The sequence of the CD44-Apt1 therefore was not trimmed.

Figure 1H:
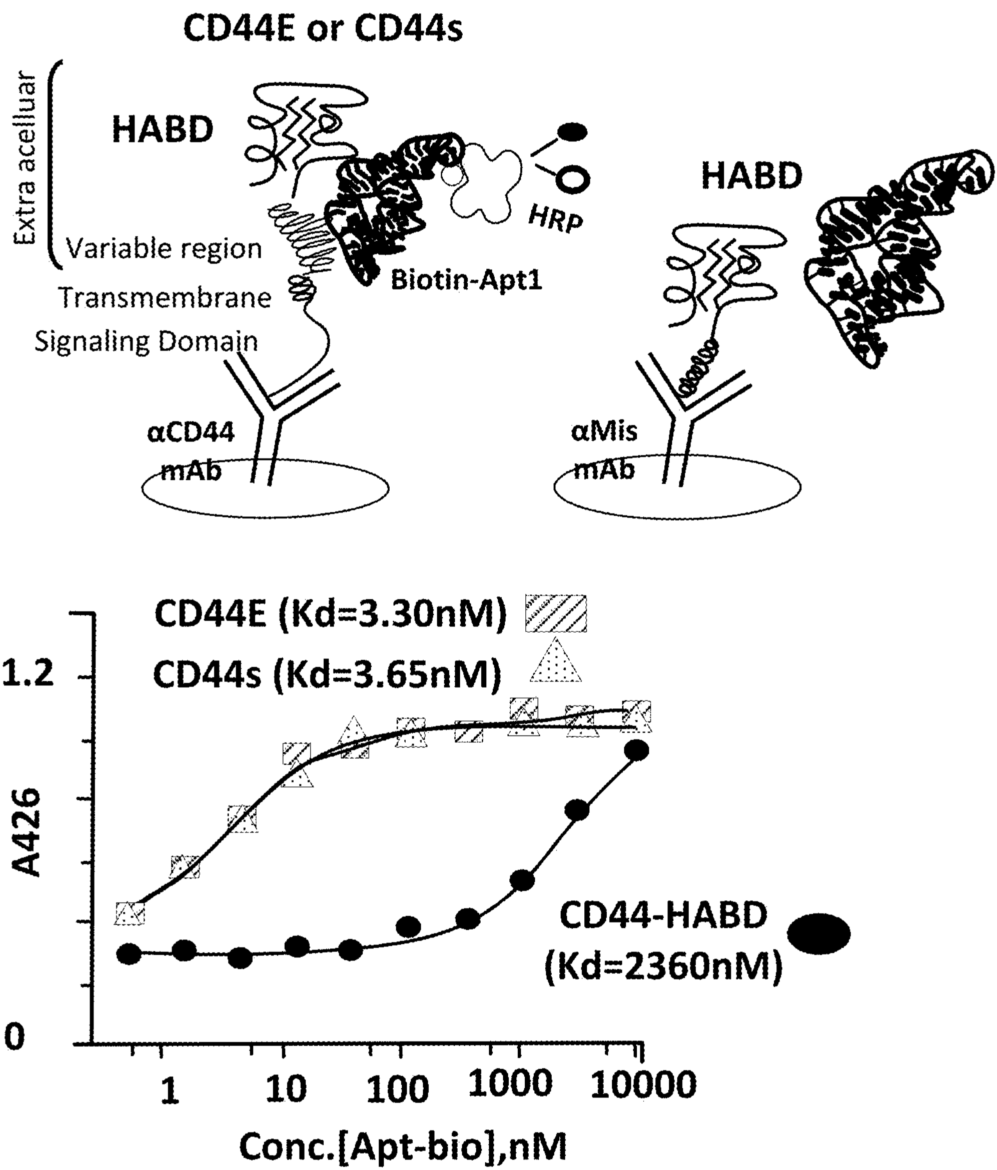
(FIG. 1H) Epitope mapping and binding affinity determination of CD44-Apt1 using sandwich ELISA. CD44E and CD44s proteins were captured on the bottom of ELISA plate using anti-CD44 antibody that targets COOH-terminal intracellular domain and remains the N-terminal extracellular domain intact for aptamer binding. His-tag recombinant CD44 HABD protein was immobilized on ELISA plate using His-tag antibody. The captured CD44 proteins were incubated with various concentrations of biotin-labeled CD44-Apt1 (5 nM-10 μM). Bound Apt1 then were detected by peroxidase-conjugated streptavidin and TMB substrate. Disequilibrium constant, $K_D$ was calculated based on the absorbance values using the one-site binding model for non-linear regression in GraphPad.

The major epitope in CD44 protein that is recognized by the CD44-Apt1 was next determined. CD44 protein consists of an extracellular domain, a transmembrane helical domain, and an intracellular signaling transmission domain (FIG. 1H). The extracellular domain contains a hyaluronic acid binding domain (HABD) at its distal N-terminus and a glycosylation-site enriched variable region, the length of which are vary in different splice variants. Titration sandwich enzyme-linked immunosorbent assay (ELISA) was employed to map the epitope for CD44-Apt1. Antibody targeting the C-terminus of CD44 proteins that is the intracellular signaling domain was immobilized on a polystyrene support. Sites without antibody were blocked using bovine serum albumin. CD44E/s proteins were captured by the CD44 antibodies on the support and non-CD44E/s components were washed off by repeated washing using Tween-containing buffer and long-time incubation between washes. On the other hand, a recombinant protein of CD44-HABD with His-tag was commercially obtained. All steps for capturing CD44-HABD on the support was as the same as that for capturing CD44E/s but via a His-tag antibody instead of the CD44 antibody. After capturing of CD44E/s or HABD on the support, a series of titrated biotin-labeled CD44-Apt1 was applied to the captured proteins and incubated. Similarly, harsh washing steps were used to wash off non-specific binding. The amount of biotin-CD44-Apt1 bound to the captured proteins were evaluated using streptavidin conjugated horseradish peroxidase (HRP) and TMB substrate. By this method, CD44-Apt1 showed strong affinity towards the CD44E/s proteins with equilibrium dissociation constant $K_D$ of 3.30 nM, while it hardly associated with the CD44-HABD protein fragment with $K_D$ of 2360 nM (FIG. 1H). Since only the extracellular domain of CD44 was exposed while both the transmembrane helix and the intracellular domain were buried when performing cell-SELEX, and the CD44-Apt1 showed weak binding affinity to the CD44-HABD, the major epitope of this aptamer was expected to be in the domain region encoded by Exon 15 to 16 (FIG. 1A).

Figure 2A:
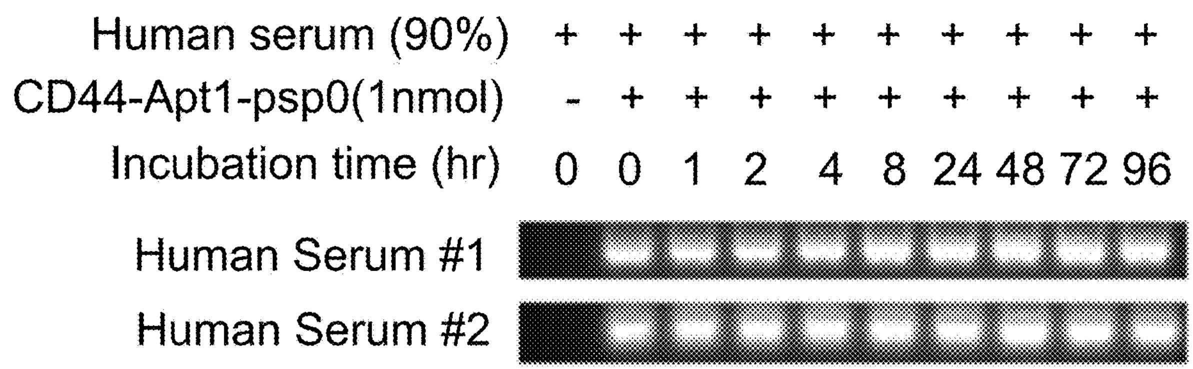
(FIG. 2A) Biostability of CD44-Apt1. One nmol of CD44-Apt1 was incubated with human serum at a ratio of 1:9 for as long as 96 hours at 37° C. and then resolved in 3% agarose gel.

Since aptamer is nucleic acid, its phosphodiester bond between nucleotides is susceptible to nuclease cleavage when exposing to biological media or in-vivo conditions. To overcome the degradation problem, the phosphodiester bonds were modified to phosphorothioate linkage by substituting the non-bridging oxygen atoms in the phosphodiester bonds to sulfur atoms[9]. The biostability of the modified CD44-Apt1 was then tested against nucleases in human serum (FIG. 2A). Human serum samples were freshly obtained from two volunteers. For each time point from 0 to 96 hours, a total of one pmol of CD44-Apt1 was incubated with the two serums separately in a dilution ratio of serum to aptamer as 9 to 1 at normal body temperature. After incubation, the mixtures were resolved by gel electrophoresis. Compared to the control at time 0, no degradation of CD44-Apt1 was observed across time. This indicated the CD44-Apt1 being highly stable when in biological media and presumably in circulation. This phosphorothioate-modified CD44-Apt1 was then used for the following in-vitro cell-based and in-vivo animal tests.

Figure 2B:
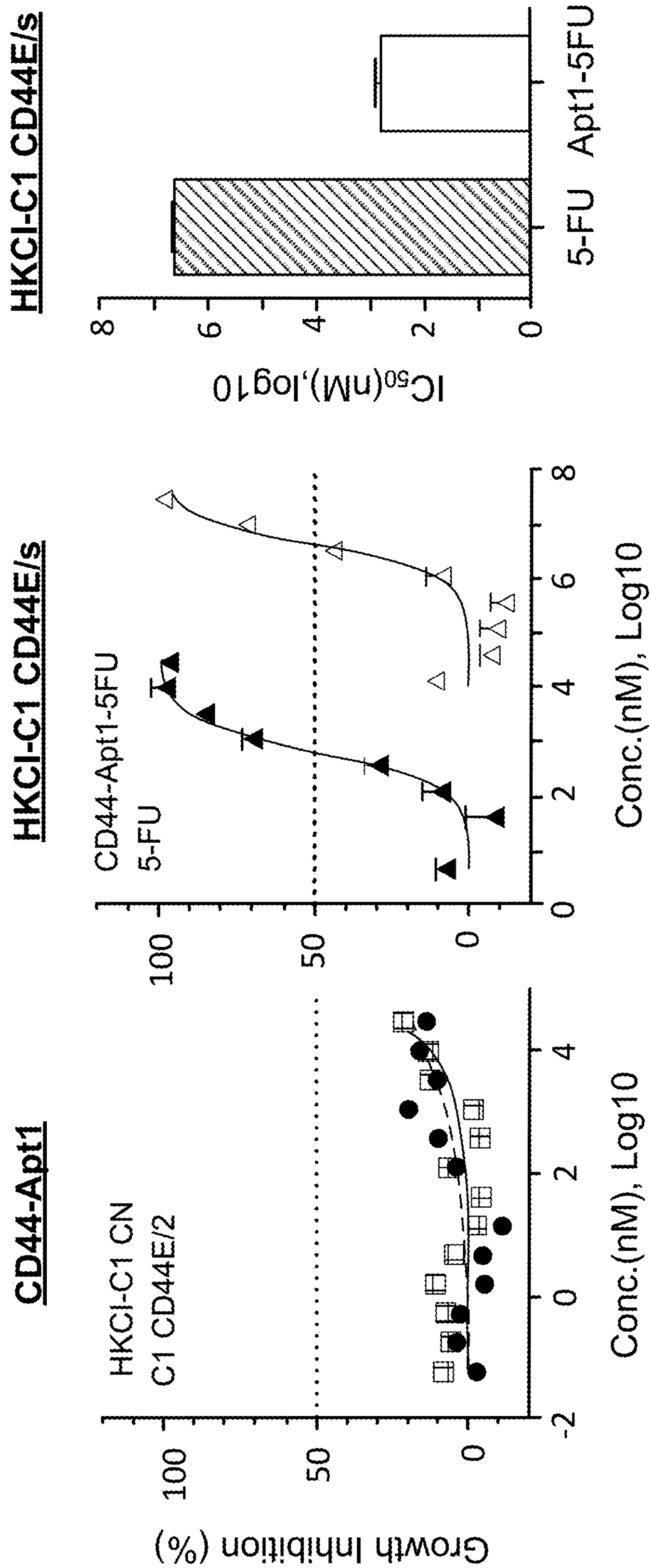
(FIG. 2B) Growth inhibition effect on HCC cells by 5-FU with or without CD44-Apt1 conjugation. HKCI-C1 control and CD44E/s cells were treated with varying concentrations of CD44-Apt15FU or 5-FU alone. Viability was measured using Celltiter-Glo, and growth inhibition percent was calculated. Half-maximal inhibitory concentration (IC50) was determined using the model of “log of inhibitor versus response with variable slope” under non-linear regression (mean±SEM, n=2).

To determine the cytotoxicity of CD44-Apt1, various concentrations of CD44-Apt1 were incubated with the HKCI-C1 CD44E/s and control cells for 72 hours and then evaluated for cell viability (FIG. 2B). With an extraordinary-high concentration at 10 μM, that is 3000-folds of the CD44-Apt1 binding affinity to CD44 proteins, more than 70% of cells were still alive after 3 days of incubation. No cell death was observed when incubating the cells with a moderate concentration of CD44-Apt1 at 1 μM. This indicates that CD44-Apt1 is non-toxic.

Figure 3A:
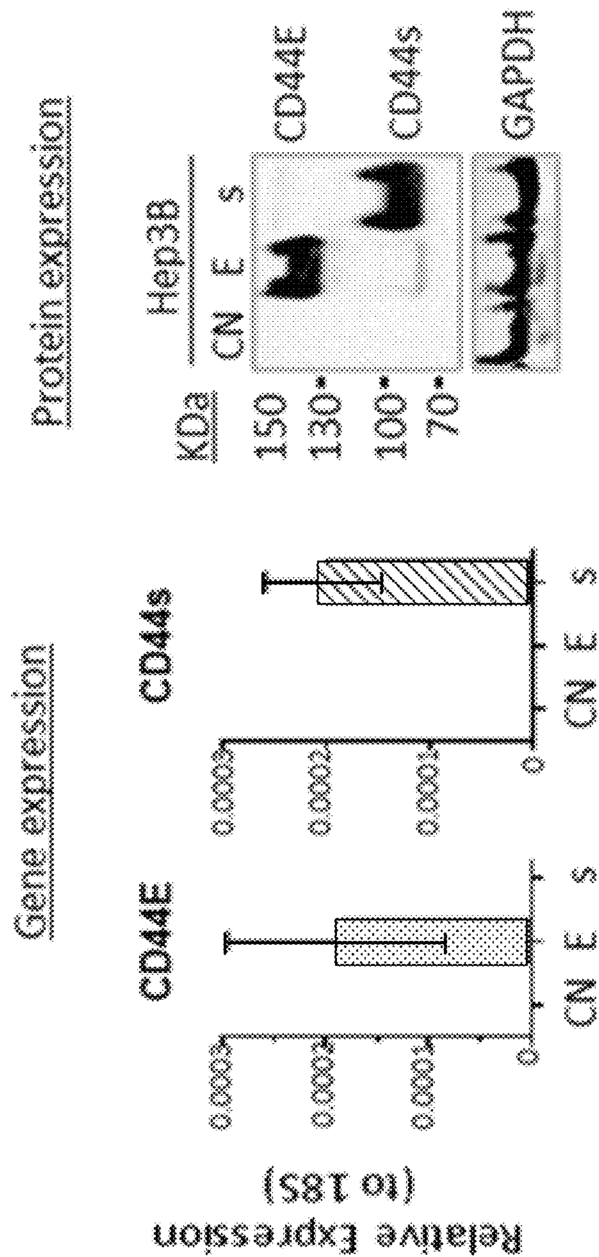
(FIG. 3A) Establishment of CD44E- and CD44s-overexpressed Hep3B stable cell lines.
Figure 3B:
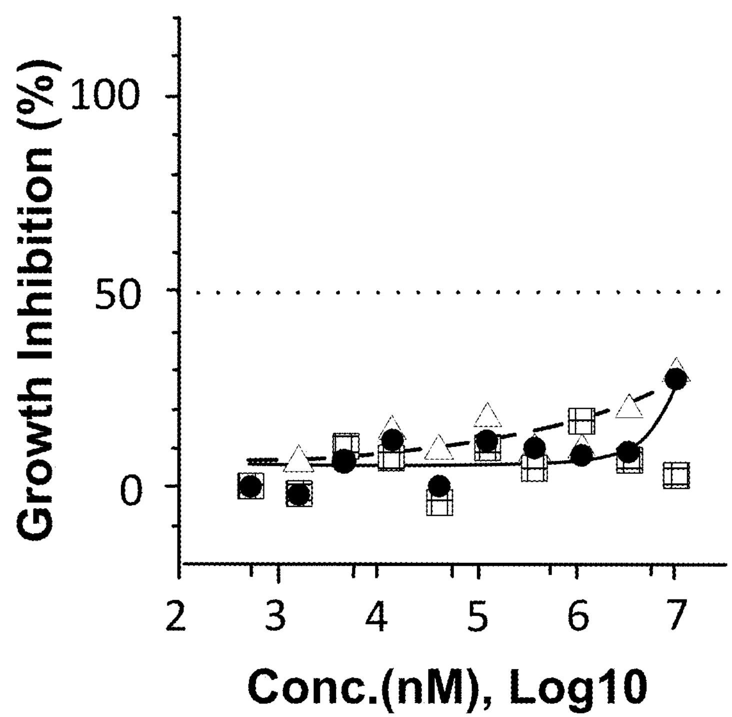
(FIG. 3B) In-vitro cytotoxicity of CD44-Apt1 on the Hep3B stable cell lines. Hep3B cells were incubated with various concentration of CD44-Apt1, ranging 56 pM to 10 μM, for 72 hours. Cytotoxicity was represented in term of percentage of growth inhibition (mean±SEM, n=3).

Anti-cancer drug fluoropyrimidine 5-fluorouracil (5-FU) is one of the most commonly used chemotherapeutic agents for treating malignant tumors, such as advanced HCC, and works by inducing DNA or RNA damages through miscorporation [10]. In clinical practice, moderate-to-high doses of 5-FU are considered necessary to achieve satisfactory anti-tumor efficacy, although the associated deleterious side effects are also common. Upregulation of CD44 had been reported in association with drug resistance to 5-FU in gastric cancer[11]. To tackle the problem of anti-cancer drug resistance, one of therapeutic strategies is to enhance drug sensitivity in cancer cells via targeting overexpressed biomarkers on the cells. This approach shows especial interest to eradicate drug resistant cells like 5-fluorouracil (5-FU) resistant tumor cells[12]. CD44-Apt1 was tested to see if it could improve drug efficacy of 5-FU on HCC cells. CD44-Apt1 was conjugated with three successive 5-FU phosphonamidites at its 3' end, designated as CD44-Apt1-5FU. HKCI-C1 cells with CD44E/s overexpression were treated at various concentrations of CD44-Apt1-5FU for 3 days. When 5-FU was applied alone, CD44E/s expressing HKCI-C1 showed a 50% growth inhibition at IC50 of 4.50±1.15mM (FIG. 3B). When guided by CD44-Apt1, CD44E/s positive HKCI-C1 showed dramatic sensitivity to CD44-Apt1-5FU with an IC50 as low as 0.66±0.16 μM. Between aptamer-guide 5FU application and 5FU alone, a clear enhanced drug sensitivity was observed with CD44-Apt1-5FU, demonstrating a reduced IC50 value by more than 6,700 folds. Taken together with the high affinity and high sensitivity features of CD44-Apt1 to CD44E/s proteins, CD44-Apt1 can work as an efficient mediator to transport anti-cancer drug, like 5-FU among others, into CD44E/s-expressing HCC tumor cells for enhanced intracellular drug loadings and thereof cytotoxic response. In addition, the dosage of anti-cancer drug could be vastly lowered to reduce adverse side-effects in patients.

Figure 3C:
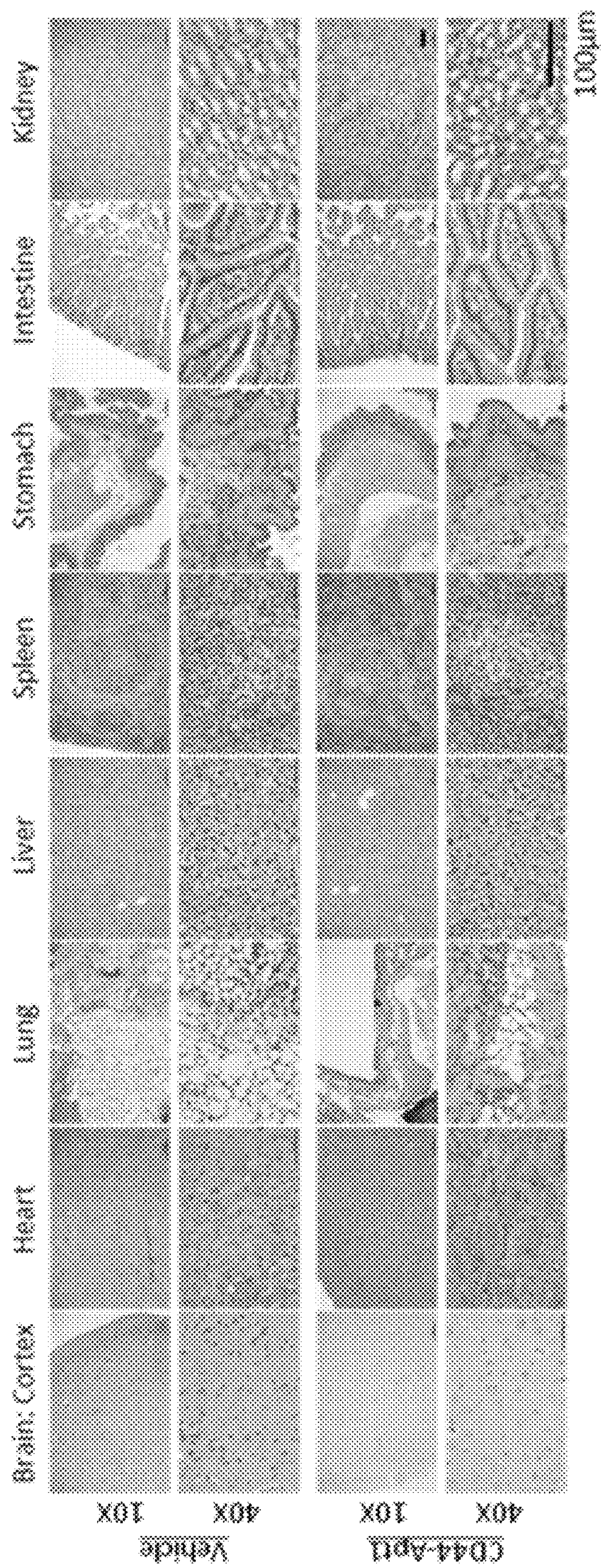
(FIG. 3C) In-vivo cytotoxicity. A total of 250 pmol of CD44-Apt1-psp0 or vehicle buffer was intravenously injected into Nude mice and incubated for 72 hours. Major organs, including prefrontal cortex of brain, heart, lung, liver, spleen, stomach, intestine and kidney were harvested and processed for haemotoxylin and eosin (H&E) staining for histological imaging.
Figure 3D:
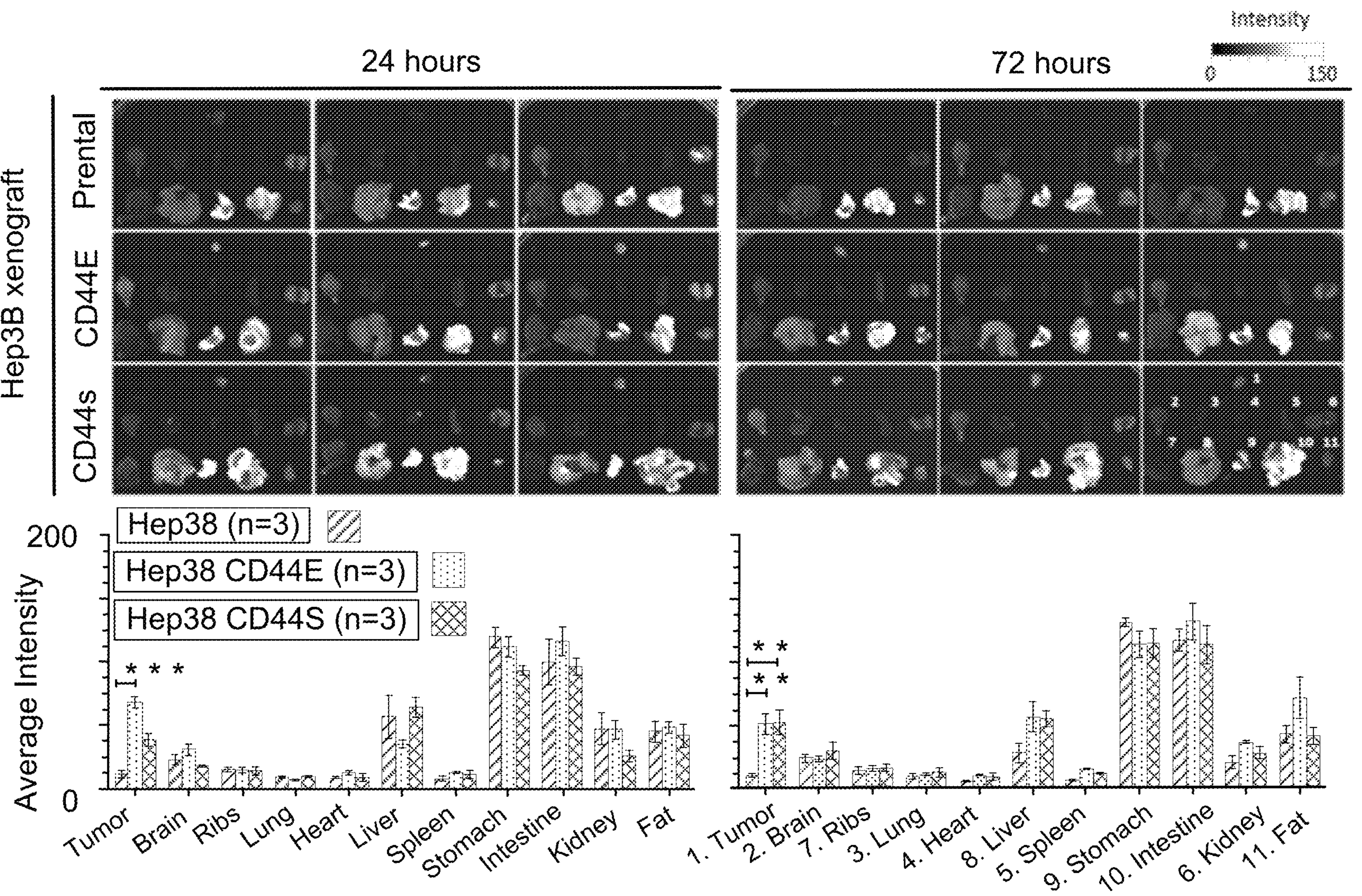
(FIG. 3D) Ex-vivo fluorescence imaging of the HCC xenograft tumor and major organs of the aptamer-injected animals. HCC xenograft tumors were developed in Nude mice by subcutaneous injection of $5\times10^6$ cells of Hep3B parental, CD44E-OE, or CD44s-OE cells. When xenograft reached size of about 200 $mm^3$, 250 pmol of Cy3-labeled CD44-Apt1 was intravenously injected into tumor-bearing mice and incubated for 24 or 72 hours before sacrifice. Fluorescence intensity was measured in the tumor and organs and compared between xenograft models using 2-way ANOVA test (mean±SEM, n=3). $^{}p<0.01$, $^{*}p<0.001$.

Efficient and specific delivery of aptamer-based therapeutics in-vivo is one the major concerns in the development of targeted therapy. Since the Hep3B cell line could be efficiently developed into xenograft model, two cell lines with overexpression of either CD44E or CD44s were generated (FIG. 3A). The CD44-Apt1 again did not induce cell death in all three Hep3B cell lines, including the parental and the two CD44-overexpressed cells (FIG. 3B). The in-vivo cytotoxicity of CD44-Apt1 was then tested. A total of 250 pmol of either CD44-Apt1 or vehicle was intravenously injected into nude mice and incubated for 3 days. Major organs, including brain, heart, lung, liver, spleen, stomach, intestine, and kidney were obtained and examined for histological differences (FIG. 3C). Histological staining showed that all harvested organs look intact and no apparent tissue damage. This result further supported the non-toxic nature of the CD44-Apt1. Next, the in-vivo homing capability of CD44-Apt1 to CD44-positive xenografts was determined. A dosage of 250 pmol of Cy3-conjugated CD44-Apt1 was intravenously injected into mice bearing xenografts that were developed by subcutaneously injection of Hep3B CD44E, CD44s, or parental cells. After 24 or 72 hours of incubation, tumor and major organs were harvested and evaluated for Cy3 signal. Significantly accumulation of Cy3 signal was observed in the CD44E xenografts as soon as at the time point of 24 hours and maintained at high level after 72 hours of incubation, while its levels in the control xenografts were barely detected at both time points. In the CD44s xenografts, CD44-Apt1 accumulation was 3-fold higher compared to that in the control xenografts after 24 hours despite not statistically significant, it subsequently elevated to a significant level after incubating 72 hours. This gradual accumulation of CD44-Apt1 in the CD44s xenografts indicates that the phosphorothioate-modified CD44-Apt1 can survive for a prolonged period under in-vivo changing physiological environment. More importantly, the Cy3 signal level in the major organs were very similar between all three xenograft models at both time points, indicating absence of non-specific binding. Taken together, CD44-Apt1 can home to the CD44-enriched HCC xenografts and can be a guiding probe in therapy.

TABLE 1

| Sequence of CD44E/s aptamer (CD44-Apt1) | |
|---|---|
| Aptamer ID | Sequence (SEQ ID NO: 1) |
| CD44-Apt1 | ATCCAGAGTGACGCAGCATCGCAACGATTAGTATGCACCCA CCGTATAGGTTGGTCTCTGGACACGGTGGCTTAGT |

The contents of all patents, patent applications, and other publications, including GenBank Accession Numbers or equivalents, cited in this application are incorporated by reference in the entirety for all purposes.

REFERENCES

[1] S. M. Nimjee, C. P. Rusconi, B. A. Sullenger, Aptamers: An Emerging Class of Therapeutics, Annu Rev Med. 56 (2005) 555-583. https://doi.org/10.1146/annurev.med.56.062904.144915.

[2] S. Yoon, J. J. Rossi, Aptamers: Uptake mechanisms and intracellular applications, Adv Drug Deliver Rev. 134 (2018) 22-35. https://doi.org/10.1016/j.addr.2018.07.003.

[3] D. Xiang, C. Zheng, S.-F. Zhou, S. Qiao, P.H.-L. Tran, C. Pu, Y. Li, L. Kong, A. Z. Kouzani, J. Lin, K. Liu, L. Li, S. Shigdar, W. Duan, Superior Performance of Aptamer in Tumor Penetration over Antibody: Implication of Aptamer-Based Theranostics in Solid Tumors, Theranostics. 5 (2015) 1083-1097. https://doi.org/10.7150/thno.11711.

[4] K. E. Maier, M. Levy, From selection hits to clinical leads: progress in aptamer discovery, Mol Ther—Methods Clin Dev. 3 (2016) 16014. https://doi.org/10.1038/mtm.2016.14.

[5] L. Kelly, C. Kratschmer, K. E. Maier, A. C. Yan, M. Levy, Improved Synthesis and In Vitro Evaluation of an Aptamer Ribosomal Toxin Conjugate, Nucleic Acid Ther. 26 (2016) 156-165. https://doi.org/10.1089/nat.2015.0599.

[6] P. K. Kulabhusan, B. Hussain, M. Yüce, Current Perspectives on Aptamers as Diagnostic Tools and Therapeutic Agents, Pharm. 12 (2020) 646. https://doi.org/10.3390/pharmaceutics12070646.

[7] Y. Morita, M. Leslie, H. Kameyama, D. E. Volk, T. Tanaka, Aptamer Therapeutics in Cancer: Current and Future, Cancers. 10 (2018) 80. https://doi.org/10.3390/cancers10030080.

[8] K. Sefah, D. Shangguan, X. Xiong, M. B. O'Donoghue, W. Tan, Development of DNA aptamers using Cell-SELEX, Nat Protoc. 5 (2010) 1169-1185. https://doi.org/10.1038/nprot.2010.66.

[9] D. E. Volk, G. L. R. Lokesh, Development of Phosphorothioate DNA and DNA Thioaptamers, Biomed. 5 (2017) 41. https://doi.org/10.3390/biomedicines5030041.

[10] D. B. Longley, D. P. Harkin, P. G. Johnston, 5-Fluorouracil: mechanisms of action and clinical strategies, Nat Rev Cancer. 3 (2003) 330-338. https://doi.org/10.1038/nrc1074.

[11] Z.-Y. Xu, J.-N. Tang, H.-X. Xie, Y.-A. Du, L. Huang, P.-F. Yu, X.-D. Cheng, 5-Fluorouracil Chemotherapy of Gastric Cancer Generates Residual Cells with Properties of Cancer Stem Cells, Int J Biol Sci. 11 (2015) 284-294. https://doi.org/10.7150/ijbs.10248.

[12] C. Sethy, C. N. Kundu, 5-Fluorouracil (5-FU) resistance and the new strategy to enhance the sensitivity against cancer: Implication of DNA repair inhibition, Biomed Pharmacother. 137 (2021) 111285. https://doi.org/10.1016/j.biopha.2021.111285.

What is claimed is:

1. An aptamer comprising the nucleotide sequence of SEQ ID NO:1 and specifically binds CD44.

2. The aptamer of claim 1, further comprising a detectable moiety.

3. The aptamer of claim 1, further comprising a therapeutic agent.

4. The aptamer of claim 1, which consists essentially of (1) the nucleotide sequence of SEQ ID NO:1 and a detectable moiety or a therapeutic agent.

5. The aptamer of claim 4, which consists of (1) the nucleotide sequence of SEQ ID NO:1 and a detectable moiety or a therapeutic agent.

6. The aptamer of claim 1, wherein the nucleotide sequence comprises at least one chemical modification.

7. The aptamer of claim 1, wherein the phosphodiester bonds in the nucleotide sequence are modified to phosphorothioate linkage by substituting the non-bridging oxygen atoms in the phosphodiester bonds to sulfur atoms.

8. The aptamer of claim 1, which is immobilized to a solid substrate.

9. The aptamer of claim 1, which binds CD44 with an equilibrium dissociation constant KD of about 3.30 nM.

10. A composition comprising the aptamer of claim 1 and a pharmaceutically acceptable excipient.

11. A method for detecting the presence of CD44-expressing cells, comprising:

(1) contacting a plurality of cells potentially comprising CD44-expressing cells with the aptamer of claim 1 under conditions permissible for specific binding between the aptamer and CD44; and (2) detecting cells specifically bound to the aptamer, thereby detecting CD44-expressing cells.

12. The method of claim 11, wherein the plurality of cells are present in a biological sample taken from a person.

13. The method of claim 11, wherein the plurality of cells are present in a person's body.

14. The method of claim 13, wherein the aptamer comprises a detectable moiety or is immobilized to a solid support.

15. The method of claim 13, further comprising, subsequent to step (2), isolating the cells specifically bound to the aptamer.

16. A method for targeted delivery to CD44-expressing cells, comprising administering to a patient in need thereof an effective amount of the aptamer of claim 1, wherein the aptamer comprises an imaging or therapeutic agent.

17. The method of claim 16, wherein the aptamer is administered systemically or locally.

18. The method of claim 16, wherein the aptamer consists essentially of SEQ ID NO:1 and the imaging or therapeutic agent.

19. The method of claim 18, wherein the therapeutic agent is an anti-cancer drug.

20. The method of claim 11, wherein the aptamer is a phosphorothioate-modified aptamer.

* * * * *

SEQUENCE LISTING

<160> NUMBER OF SEQ ID NOS: 3

<210> SEQ ID NO 1
<211> LENGTH: 76
<212> TYPE: DNA
<213> ORGANISM: Artificial Sequence
<220> FEATURE:

-continued

```
<223> OTHER INFORMATION: Description of Artificial Sequence: Synthetic
      oligonucleotide

<400> SEQUENCE: 1

atccagagtg acgcagcatc gcaacgatta gtatgcaccc accgtatagg ttggtctctg     60

gacacggtgg cttagt                                                     76


<210> SEQ ID NO 2
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 2

cctgctacca atatggactc                                                 20


<210> SEQ ID NO 3
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 3

cctgctacca gagaccaaga                                                 20
```